United States Patent [19]
Spector et al.

[11] Patent Number: 6,013,623
[45] Date of Patent: Jan. 11, 2000

[54] USE OF HEME-PEPTIDES TO PREVENT OR RETARD DISEASE ASSOCIATED WITH OXIDATIVE STRESS

[75] Inventors: Abraham Spector; Wanchao Ma; Ren-Rong Wang, all of New York, N.Y.

[73] Assignee: The Trustees of Columbia University in the City of New York, New York, N.Y.

[21] Appl. No.: 08/807,482

[22] Filed: Feb. 27, 1997

[51] Int. Cl.[7] .......................... A61K 38/00; A61K 38/16; C07K 5/00; C07K 7/00

[52] U.S. Cl. ................... 514/6; 514/12; 514/15; 514/16; 514/21; 530/304; 530/326; 530/327; 530/328; 530/400; 530/401

[58] Field of Search .................. 514/6, 12, 15, 514/16, 21; 530/304, 326, 327, 328, 400, 401

[56] References Cited

U.S. PATENT DOCUMENTS 5,696,109 12/1997 Malfroy-Camine ............. 514/185

OTHER PUBLICATIONS

Abraham, Nader G. et al. (1995) Adenovirus–Mediated Heme Oxygenase–1 Gene Transfer Into Rabbit Ocular Tissues. *Investigative Ophthalmology & Visual Science* 36:2202–2210(Exhibit A).

Ames, Bruce N. et al. (1993) Oxidants, antioxidants, and the degenerative diseases of aging Proc. Natl. Acad. Sci. 90:7915–7922(Exhibit B).

Bodaness, Richard S. et al. (1984) An analysis of the $H_2O_2$–Mediated Crosslinking of Lens Crystallins Catalyzed by the Heme–Undecapeptide from Cytochrome c. *Archives of Biochemistry and Biophysics* 231:461–469(Exhibit C).

Bodaness, Richard S. et al. (1983) The rapid $H2O2$–mediated nonphotodynamic crosslinking of lens crystallins generated by the heme–unadecapeptide from cytochrome C: Potential implications for cataractogenesis in man. Biochemical and Biophysical Research Communications 113:592–597(Exhibit D).

Elstner, E.F. (1991) Oxygen Radicals—Biochemical Basis for their Efficacy, *Klinische Wochenschrift* 69:949–956(Exhibit E).

Kikugawa, Kiyomi et al. (1991) Development of fluorescence and cross–links in eye lens crystallin by interaction with lipid peroxy radicals. *Biochemica et Biophysica Acta* 1906; 108–114(Exhibit F).

Lysko, A.I. et al. (1990) The mechanism of the antioxidant effect of cytochrome C heme nonapeptide. *Dokl Akad Nauk SSSR* 315(2);500–504(Exhibit G).

Reddan, John R. et al. (1996) Regional differences in the distribution of catalase in the epithelium of the ocular lens. *Cellular and Molecular Biology* 42(2): 209–219(Exhibit H).

Feng Xu et al, *Biochn. Biophys. Res. Comm.*, vol. 181, No. 1 pp. 197–203, Nov. 1991.

Spector et al., *Exp. Eye. Res.*, vol. 65, pp. 457–470, 1997.

Lysko et al. *Dokl Akad Nauk SSSR.*, 315 (2) (1990), 500–504.

*Primary Examiner*—Avis M. Davenport
*Attorney, Agent, or Firm*—John P. White; Cooper & Dunham LLP

[57] ABSTRACT

This invention provides a method for treating a condition associated with oxidative stress in a subject which comprises administering to the subject an amount of a heme-peptide effective to treat the condition associated with oxidative stress in the subject. The subject may be a mammal. The mammal may be a human being. The condition associated with oxidative stress may be an inflammatory condition, an allergic condition or an auto-immune condition.

53 Claims, 17 Drawing Sheets

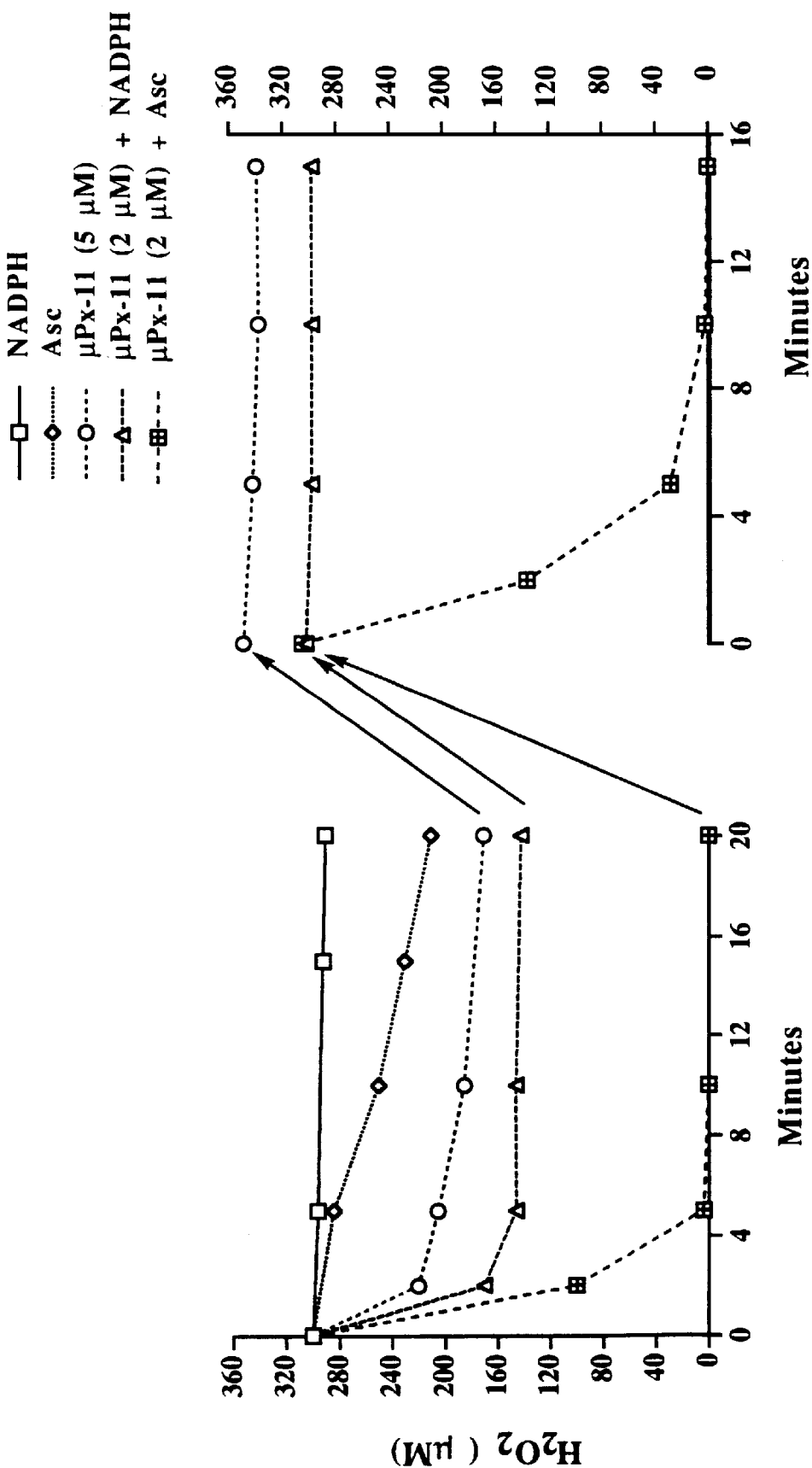

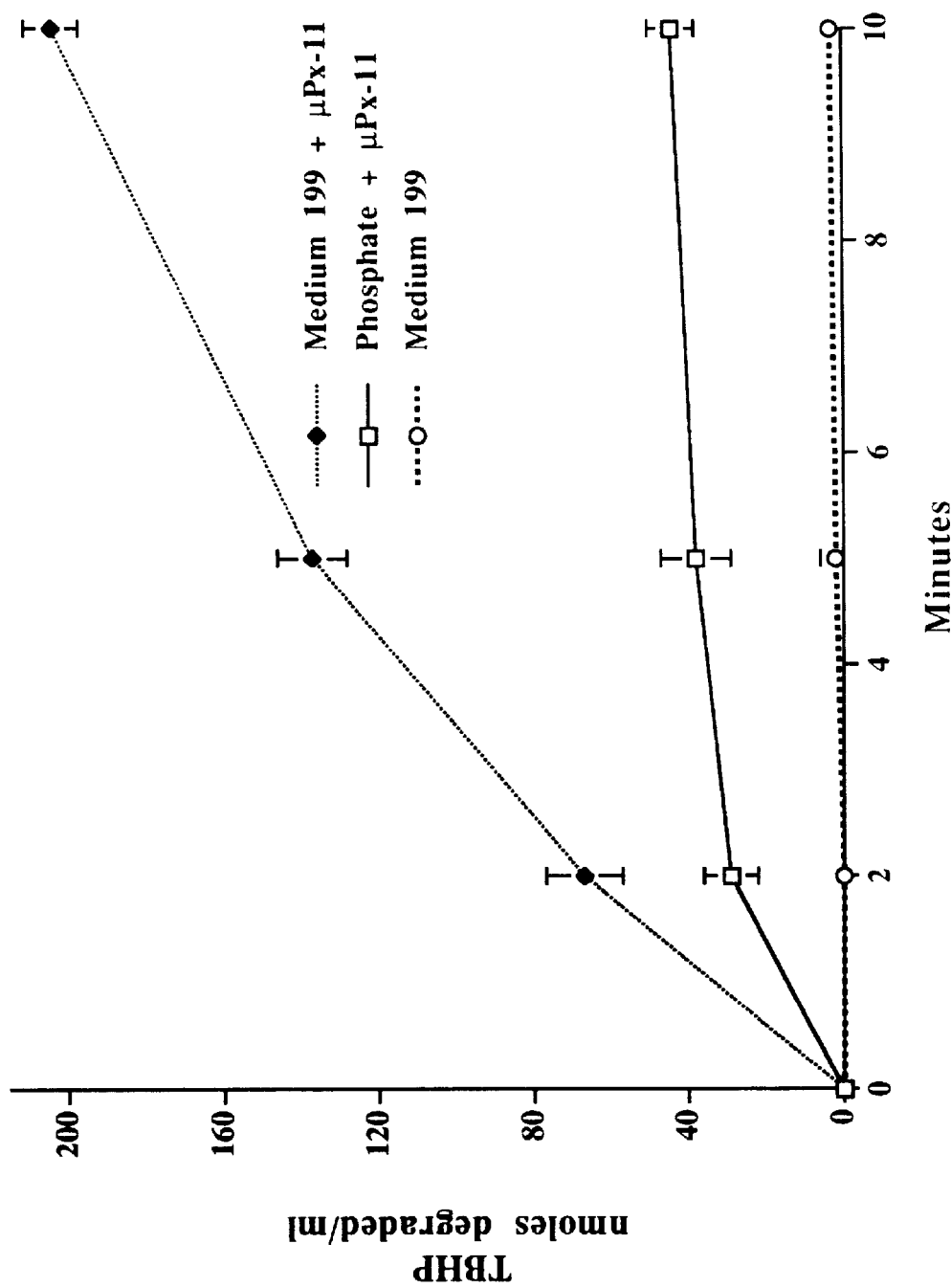

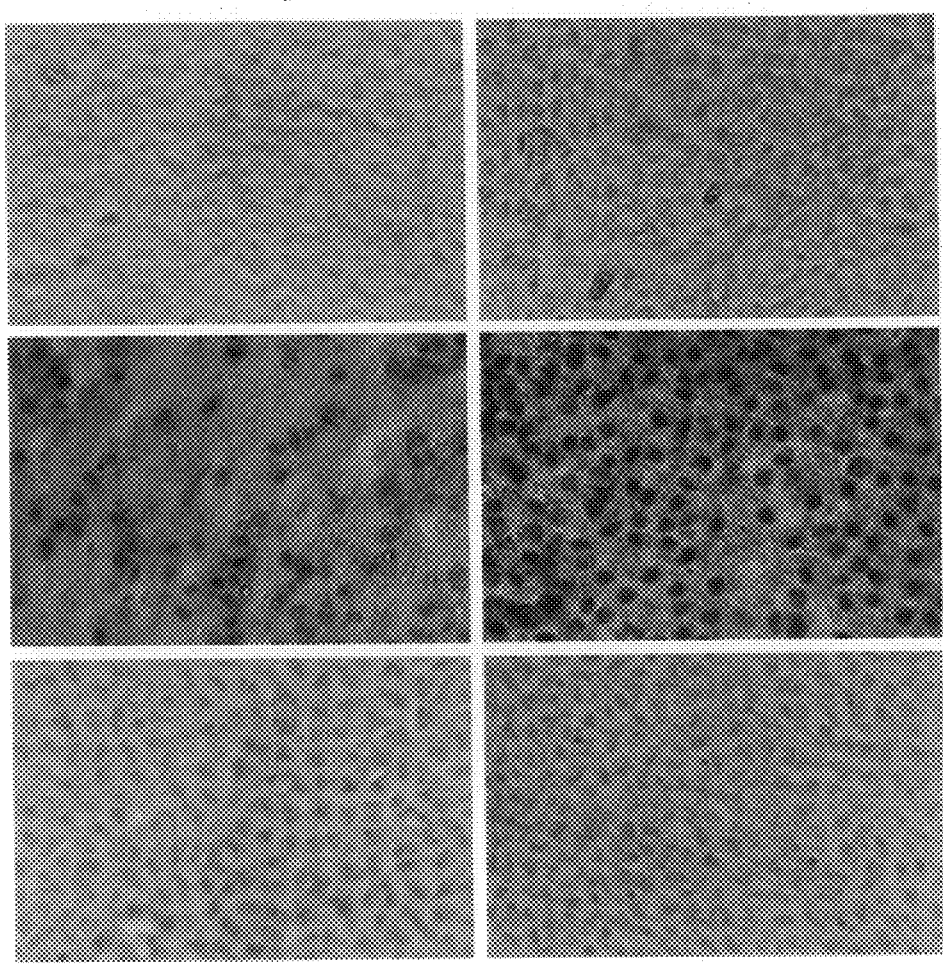

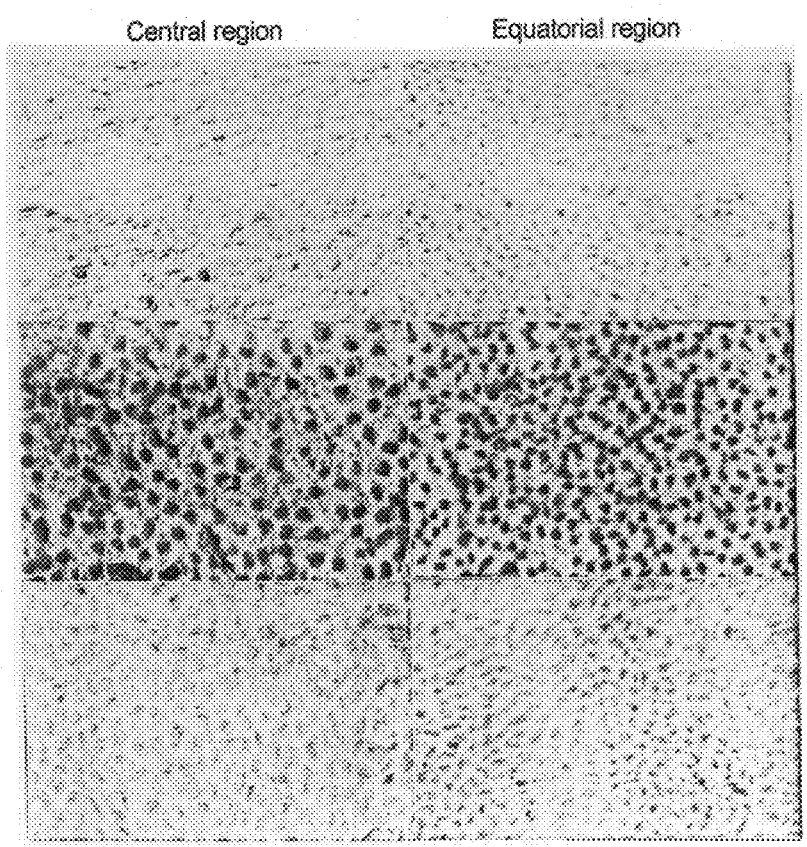

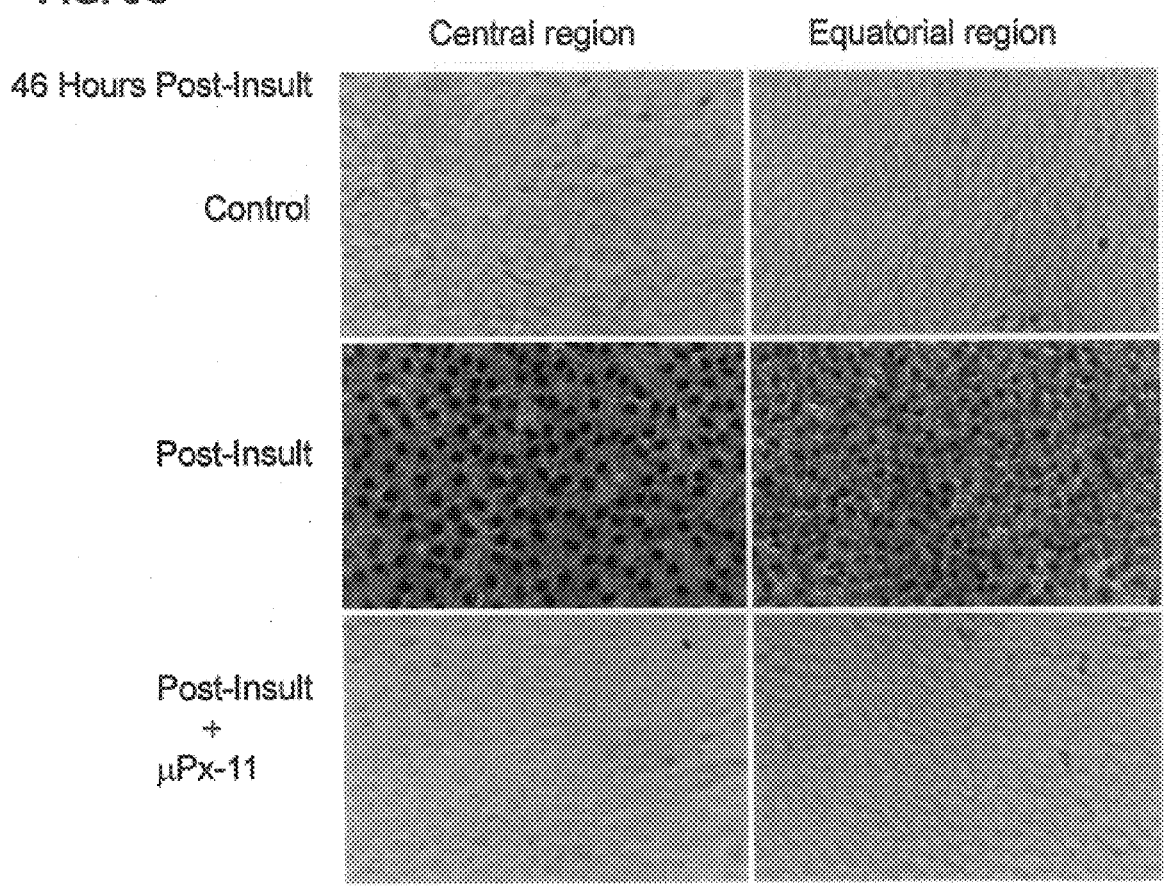

USE OF HEME-PEPTIDES TO PREVENT OR RETARD DISEASE ASSOCIATED WITH OXIDATIVE STRESS

BACKGROUND OF THE INVENTION

Throughout this application, various publications are referenced by author and date. Full citations for these publications may be found listed alphabetically at the end of the specification immediately preceding the sequence listing. The disclosures of these publications in their entireties are hereby incorporated by reference into this application in order to more fully describe the state of the art as known to those skilled therein as of the date of the invention described and claimed herein.

It has been established that oxidative stress is associated with the development of cataract and it is generally believed that $H_2O_2$ is the major oxidant producing this stress (Spector, 1995). Therefore, it would be constructive to produce a compound that would effectively eliminate $H_2O_2$ in biological materials. However, efforts to produce such compounds have only been partially successful. Utilizing, as a model, reduced glutathione (GSH), glutathione peroxidase (GSHPx), a selenoenzyme which degrades $H_2O_2$, attempts have been made to develop synthetic GSHPx mimics. A number of such selenium centered mimics have been synthesized, such as Ebselen and 2,2'diselenobis (N,N dimethylamino)methyl benzene (Wendel, 1985; Wilson et al., 1989). While these compounds have considerable GSHPx like activity, they have been found to be toxic in the $\mu M$ (micromolar) range required for effective activity based on lens epithelial cell culture viability studies. Furthermore, GSHPx-1 (the major glutathione peroxidase) transgenic mice, where the lens GSHPx-1 activity has been increased 4 to 5 fold, were found to be no more effective than normal lenses in metabolizing $H_2O_2$ (Spector et al., 1996). This was found to be due to the limiting activity of GSSG Red (oxidized glutathione reductase) which is required to maintain GSH, a cofactor for the enzyme. In contrast to the GSHPx-1 results, increasing catalase activity (another peroxide degrading enzyme) in transfected lens epithelial cell cultures significantly increased $H_2O_2$ degradation and the cell's ability to withstand oxidative stress (Spector et al., 1996).

SUMMARY OF THE INVENTION

This invention provides a method for treating a condition associated with oxidative stress in a subject which comprises administering to the subject an amount of a heme-peptide effective to treat the condition associated with oxidative stress in the subject. The subject may be a mammal. The mammal may be a human being. The condition associated with oxidative stress may be an inflammatory condition, an allergic condition or an auto-immune condition.

BRIEF DESCRIPTION OF THE FIGURES

FIGS. 1A–1C. Activity and stability of microperoxidase-11 ($\mu Px$-11).

(FIG. 1A) Effect of cofactors on $\mu Px$-11 degradation of $H_2O_2$. 300 $\mu M$ hydrogen peroxide ($H_2O_2$) was incubated with $\mu Px$-11 in 50 mM phosphate buffer, pH 7.0 at 25° C. in 1 ml. At indicated times, 50 $\mu l$ aliquots were removed for $H_2O_2$ assay as described in the Materials and Methods section. 50 mM phosphate buffer, pH 7.0 buffer+500 $\mu M$ NADPH, buffer+1 mM ascorbate (Asc), buffer+3 $\mu M$ ($\mu Px$-11), prior solution+500 $\mu M$ NADPH, as the previous solution but with 1 mM Asc rather than NADPH. 20 $\mu M$ $\mu Px$-11 in 50 mM phosphate buffer pH 7.0. The results represent the average±S.D. of 3 experiments in most cases.

(FIG. 1B) Stability of $\mu Px$-11 as measured by ability to degrade $H_2O_2$. 300 $\mu M$ $H_2O_2$ in 2 ml of 50 mM phosphate buffer, pH. 7.0 was used with noted additions under the following conditions. At indicated times, 50 $\mu l$ aliquots were removed for $H_2O_2$ assay. At 20 minutes, 1 ml of the various preparations was removed. The levels of certain components ($H_2O_2$, NADPH or Asc) were brought back to estimated starting concentrations based on prior experiments and the $H_2O_2$ decay again measured. 500 $\mu M$ NADPH, 1 mM Asc, 5 $\mu M$ $\mu Px$-11, 2 $\mu M$ $\mu Px$-11+500 $\mu M$ NADPH, 2 $\mu M$ $\mu Px$-11+1 mM Asc. The results represent a typical experiment.

(FIG. 1C) Concentration dependence of $\mu Px$-11 in the presence of Asc. The activity of 1 $\mu M$ $\mu Px$-11 in 50 mM phosphate pH 7.0, 1 mM Asc was examined at different concentrations of $H_2O_2$ at 25° C. Results were corrected for spontaneous reaction with Asc. The data is expressed as nmoles $H_2O_2$ degraded per ml per minute per nmole $\mu Px$-11 in 1 ml. The initial $H_2O_2$ degradation rate measured in the first minute is given. The results are the average±S.D. of 2 experiments.

The degradation of 300 $\mu M$ $H_2O_2$ by 3 $\mu M$ $\mu Px$-11 in a number of different media at pH 7.0, 25° C. was followed by removing 50 $\mu l$ aliquots at the designated times and assaying for $H_2O_2$ as noted in the Materials and Methods section: medium 199, bovine aqueous humor, 50 mM phosphate+ $\mu Px$-11, bovine aqueous humor+$\mu Px$-11, 50 mM phosphate+1 mM Asc+$\mu Px$-11, medium 199+$\mu Px$-11. See Experimental Details section for description of medium 199. Results are the average±S.D. of 2 experiments.

Figure 3A:
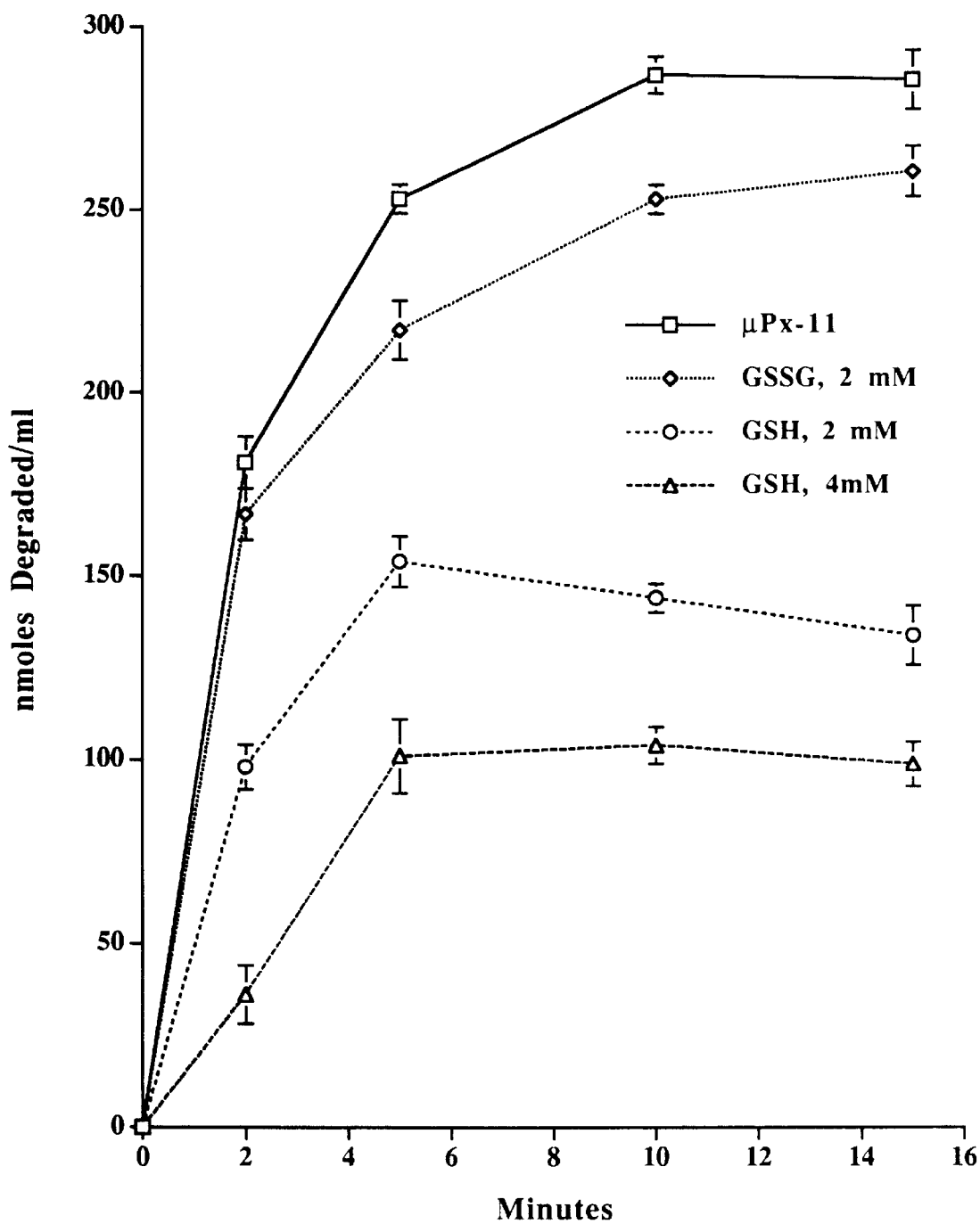
Figure 3B:
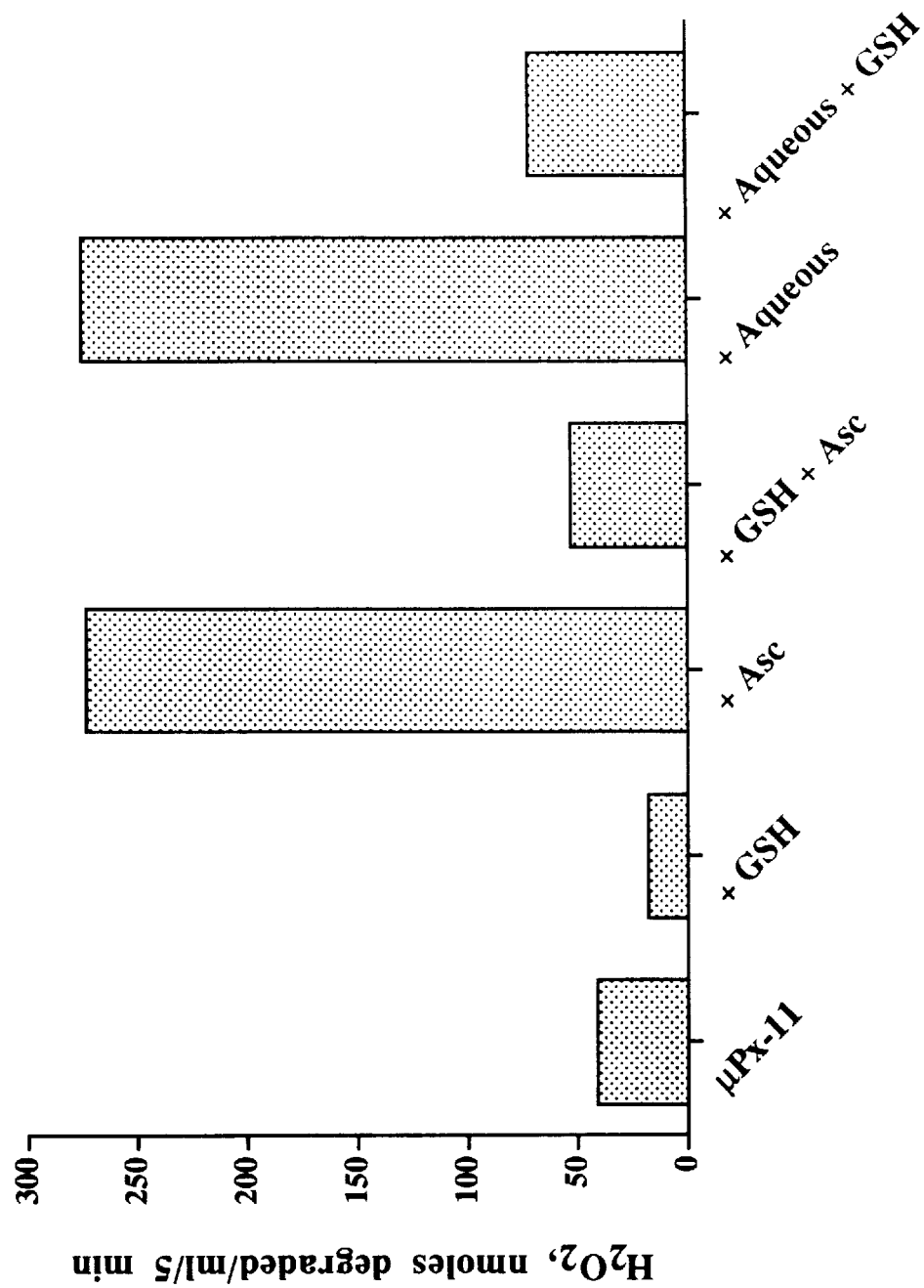

FIGS. 3A–3B. The effect of glutathione on $\mu Px$-11.

(FIG. 3A) The effect of glutathione on $\mu Px$-11 activity in the absence of cofactors. The degradation of $H_2O_2$, 300 $\mu M$ by 20 $\mu M$ $\mu Px$-11 in phosphate buffer, 50 mM, pH 7.0 at 25° C. was followed in the presence of varying concentrations of GSH and also with GSSG. The reported experiments containing GSH were corrected for the spontaneous reduction of $H_2O_2$.$\mu Px$-11, $\mu Px$-11+2 mM GSSG, $\mu Px$-11+2 mM GSH, $\mu Px$-11+4 mM GSH. The results are the average±S.D. of 2 experiments.

(FIG. 3B) The influence of Asc and varied media on the GSH effect upon $\mu Px$-11 activity. $\mu Px$-11, 3 $\mu M$ was added to 300 $\mu M$ $H_2O_2$ under different conditions at 25° C. and the degradation of $H_2O_2$ occurring in 5 minutes was determined. $\mu Px$-11 was measured in 50 mM phosphate buffer, pH 7.0 alone or with addition of 1 mM GSH, 1 mM Asc, 1 mM GSH+1 mM Asc and also alone in bovine aqueous humor adjusted to pH 7.0 and with addition of 1 mM GSH. The results are corrected for spontaneous $H_2O_2$ digestion in the absence of $\mu Px$-11. The results represent a typical experiment.

Figure 4:
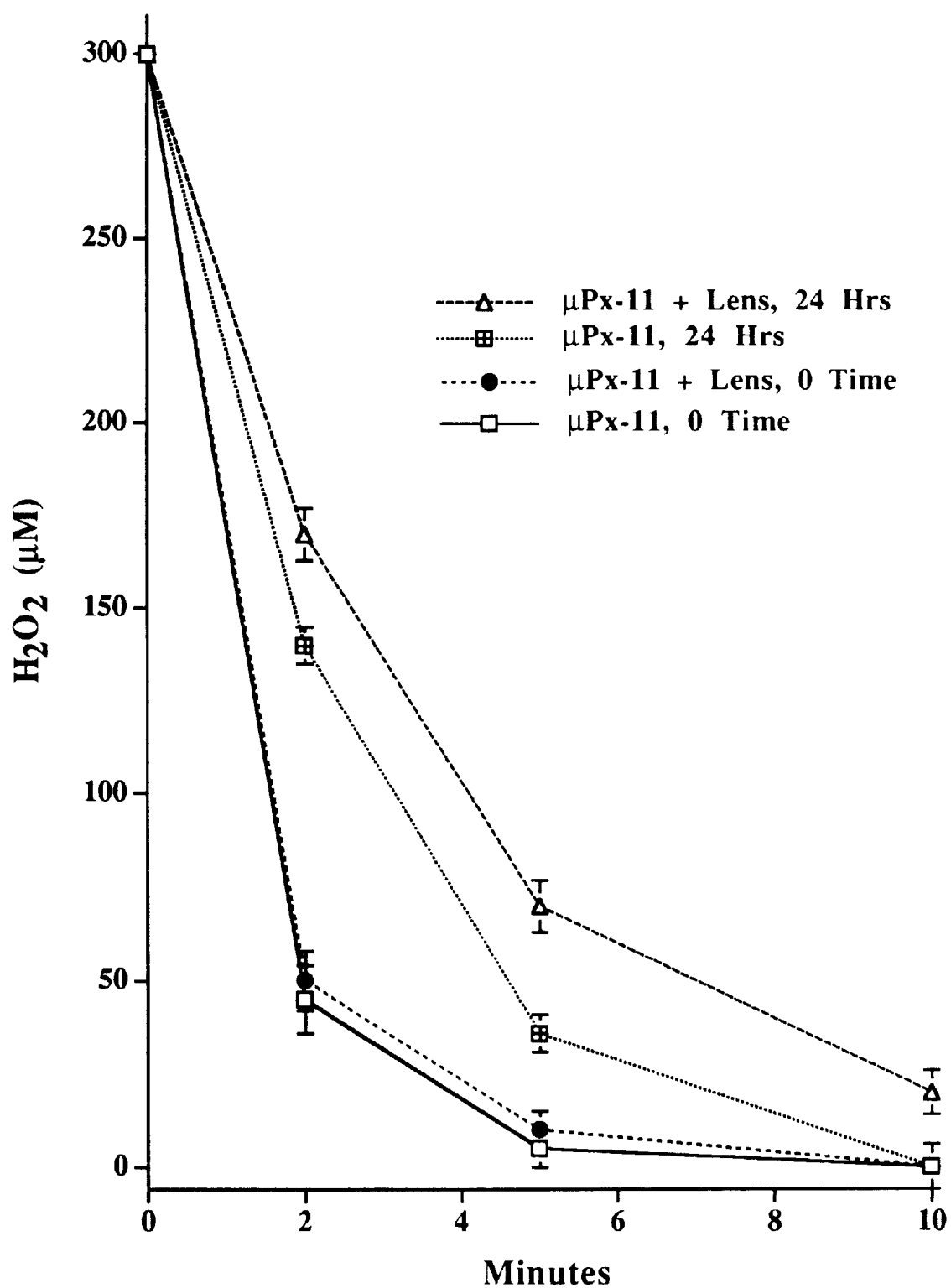

FIG. 4. The effect of the rat lens on $\mu Px$-11 activity.

A five to six week old rat lens was added to 250 $\mu l$ of medium 199 containing 20 $\mu M$ $\mu Px$-11, 1 mM Asc, 25 mM Hepes, 10.7 mM $NaHCO_3$. 0.69 mM glutamine, penicillin, 50 unit/ml, streptomycin, 50 $\mu g$/ml, final pH 7.0. All lenses were preincubated for 24 hours before initiating the experiment. When $\mu Px$-11 was used, the preincubation medium contained 20 $\mu M$ $\mu Px$-11. 100 $\mu l$ aliquots of the medium were then removed at zero time and at 24 hours and the ability to degrade $H_2O_2$ determined at a 2 $\mu M$ $\mu Px$-11 level in 50 mM phosphate, pH 7.0, 1 mM Asc 25° C., 300 $\mu M$ $H_2O_2.\mu Px$-11+lens incubated 24 hours before assay, $\mu Px$-11 incubated 24 hours without a lens, $\mu Px$-11+lens 0 time values, $\mu Px$-11 0 time values. The results are the average±S.D. of 2 experiments.

Figure 5:
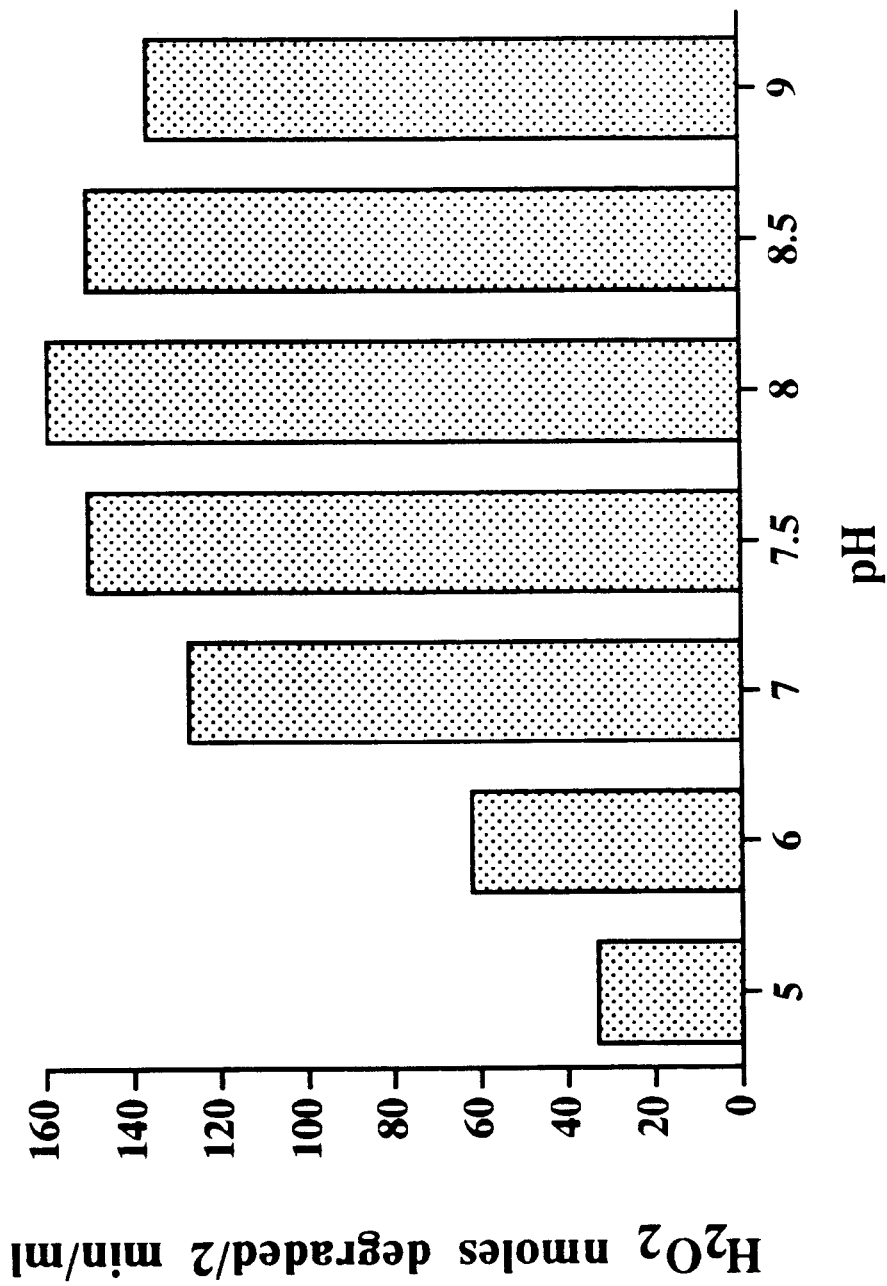

FIG. 5. $\mu Px$-11 pH optimum.

$\mu Px$-11, 1 $\mu M$ was assayed at the indicated pHs in 1 ml of medium 199 solution (see FIG. 4 for composition) at 25° C. containing 300 $\mu M$ $H_2O_2$. 50 $\mu l$ aliquots were assayed after 2 minutes. FIG. 5 shows the results of a typical experiment.

Figure 6B:
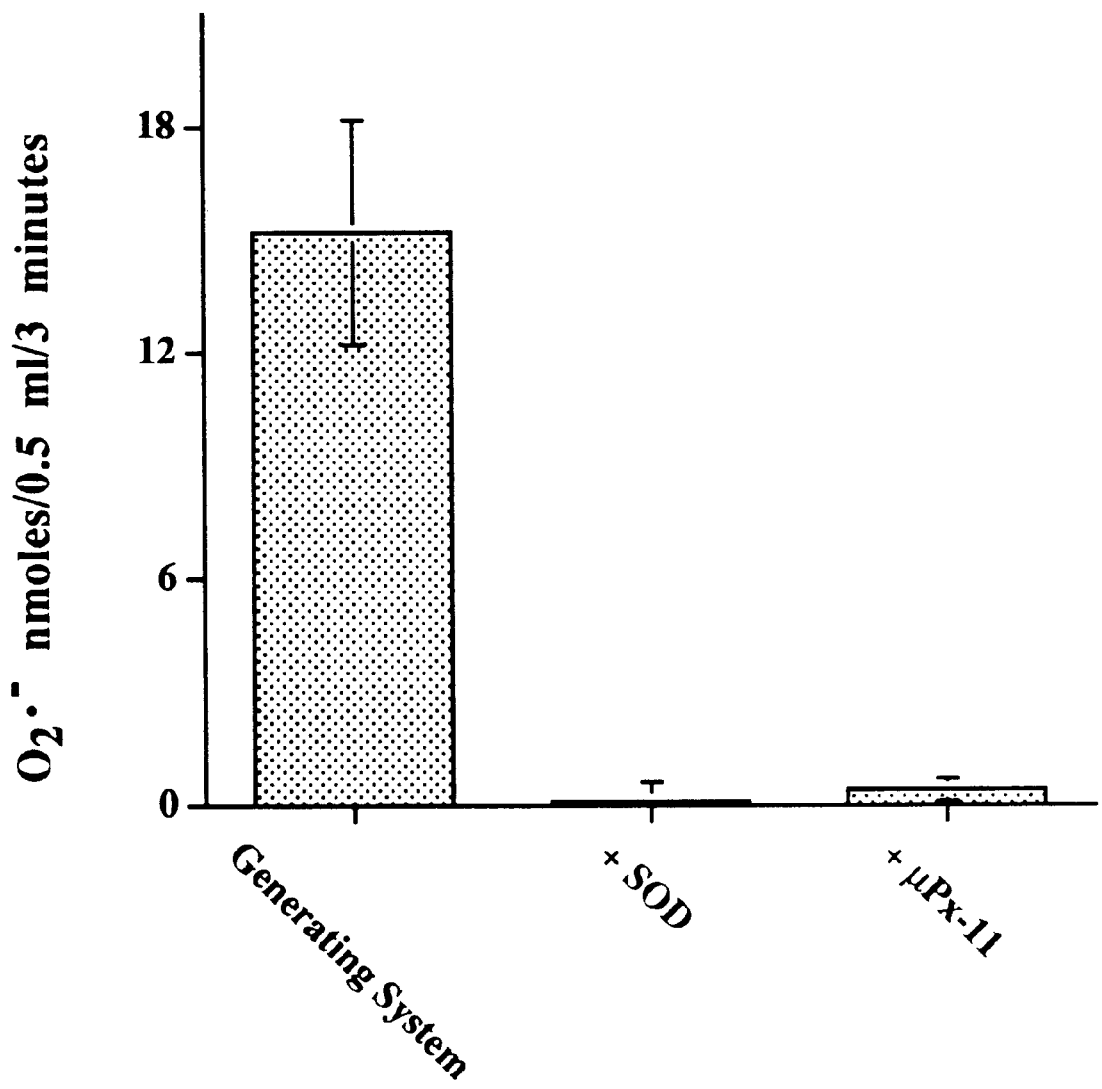
Figure 6C:
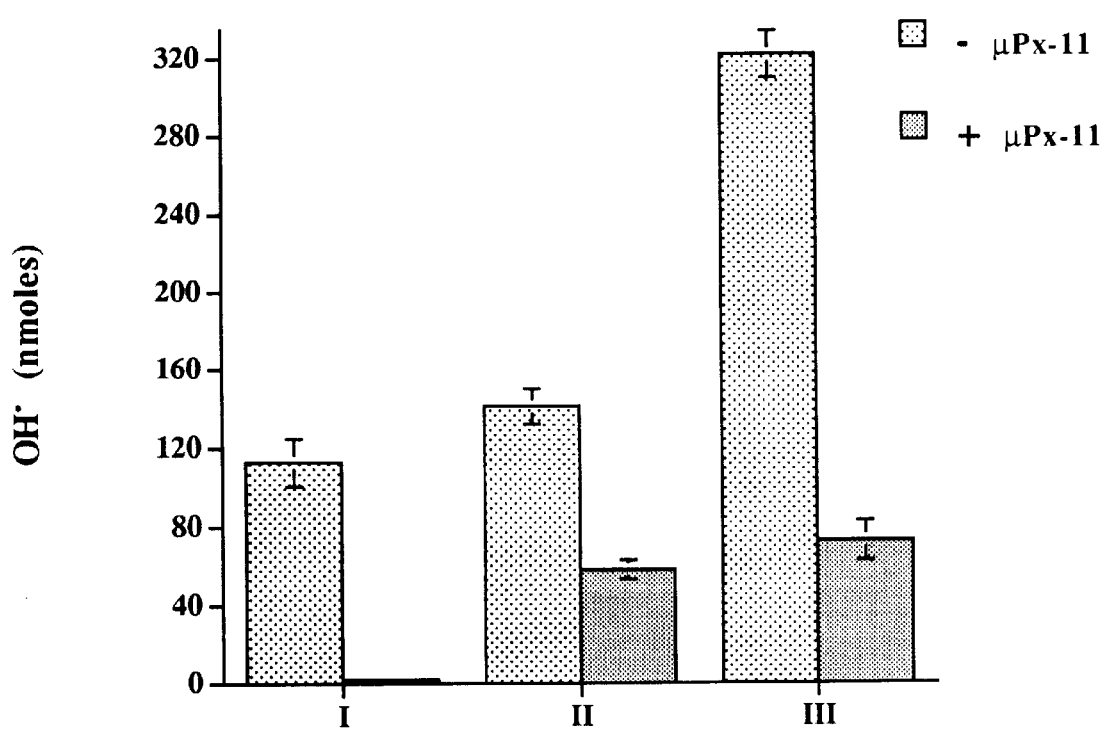

FIGS. 6A–6C. Degradation of TBHP (tertiary butyl hydroperoxidase), superoxide and hydroxyl radical by $\mu Px$-11.

(FIG. 6A) Digestion of TBHP by $\mu Px$-11. 1 ml of 300 $\mu M$ TBHP in 50 mM phosphate, pH 7.0 or medium 199, pH 7.0 (see FIG. 4 for composition) was digested by 5 $\mu M$ $\mu Px$-11. 50 $\mu l$ aliquots were taken at indicated times and assayed for $H_2O_2$ in the same manner as previously described: medium 199+5 $\mu M$ $\mu Px$-11, phosphate+5 $\mu M$ $\mu Px$-11, medium 199. The results are the average±S.D. of 2 experiments.

(FIG. 6B) Degradation of $O_2.^-$ by $\mu Px$-11. $O_2.^-$ was generated by 50 $\mu M$ xanthine, 15 mU xanthine oxidase and trapped by 25 $\mu M$ ferricytochrome C. The effect of SOD, 50 units and 5 $\mu M$ $\mu Px$-11 were examined in 0.5 ml solutions containing 50 mM phosphate, pH 7.0, 0.1 mM EDTA. The superoxide trapped at 3 minutes is shown. The results are the average±S.D. of 2 experiments.

(FIG. 6C) The effect of 5 $\mu M$ $\mu Px$-11 on OH. levels. OH. was generated by three systems. I. hypoxanthine/xanthine oxidase, II Asc and III Asc/$H_2O_2$. The reactions were carried out in 2 ml of phosphate buffer, 150 mM, pH 7.4. 2.5 mM salicylate was used to trap the OH. and the amount detected in 90 minutes, system I or 30 minutes, system II and III is shown. See Materials and Methods and the Experimental Details section. The results are the average±S.D. of 2 experiments.

Figure 7:
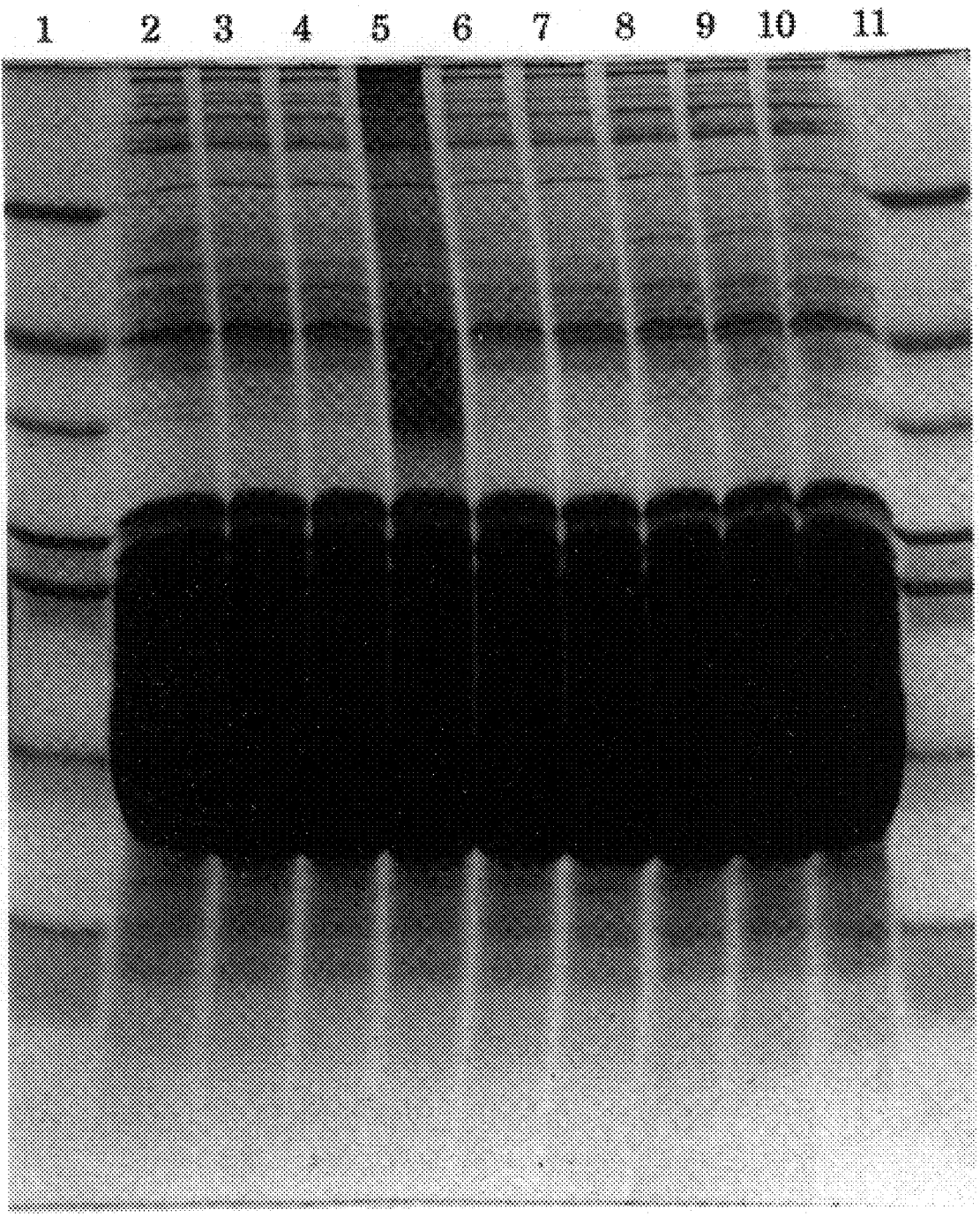

FIG. 7. The effect of $\mu Px$-11 on lens protein determined by SDS-PAGE.

Rat lens soluble protein was subjected for 30 min to 4 $\mu M$ $\mu Px$-11 in 10 mM phosphate buffer, pH 7.0 at 37° C. In certain cases, 200 $\mu M$ $H_2O_2$, 1 mM Asc and 4 mM GSH were added as indicated. In some experiments, the lens was first incubated in 150 $\mu l$ of the usual medium 199 (see FIG. 4) containing 20 $\mu M$ $\mu Px$-11 at 37°, in 5% $CO_2$ for 24 hours. The medium was then changed to 2 ml medium 199, 300 $\mu M$ $H_2O_2$±5 $\mu M$ $\mu Px$-11±1 mM Asc. After 30 minutes, the lens was washed with isotonic saline and homogenized in 20 mM phosphate pH 7.0 at 0° C. The soluble protein was then prepared for SDS-PAGE and analyzed as described in the Materials and Methods section. Lanes 1 and 11—standards: α-lactalbumin 14,200 Daltons (Da), trypsin inhibitor—20,100 Da, trypsinogen—24,000 Da, carbonic anhydride—29,000 Da, glyceraldehyde-3-phosphate dehydrogenase—36,000 Da, egg albumin—45,000 Da, and bovine-albumin—66,000 Da. Lane 2—soluble lens protein treated with 200 $\mu M$ $H_2O_2$ for 30 minutes. Lane 3—soluble lens protein treated with 4 $\mu M$, $\mu Px$-11 for 30 minutes. Lane 4—soluble lens protein. Lane 5—soluble lens protein treated with 4 $\mu M$ $\mu Px$-11 and 200 $\mu M$ $H_2O_2$ for 30 minutes. Lane 6—soluble lens protein+4 $\mu M$ $\mu Px$-11, 1 mM Asc, and 200 $\mu M$ $H_2O_2$ incubated for 30 minutes. Lane 7—soluble lens protein+4 $\mu M$ $\mu Px$-11+4 mM GSH+200 $\mu M$ $H_2O_2$ after 30 minute incubation. Lane 8—soluble protein from lens incubated in medium 199 for 24 hours. Lane 9—as lane 8 but lenses were exposed to 20 $\mu M$ $\mu Px$-11 during 24 hour incubation and then incubated an additional 30 minutes in 300 $\mu M$ $H_2O_2$ in presence of 5 $\mu M$ $\mu Px$-11. Lane 10—as lane 9+1 mM Asc during final 30 minute incubation.

Figure 8:
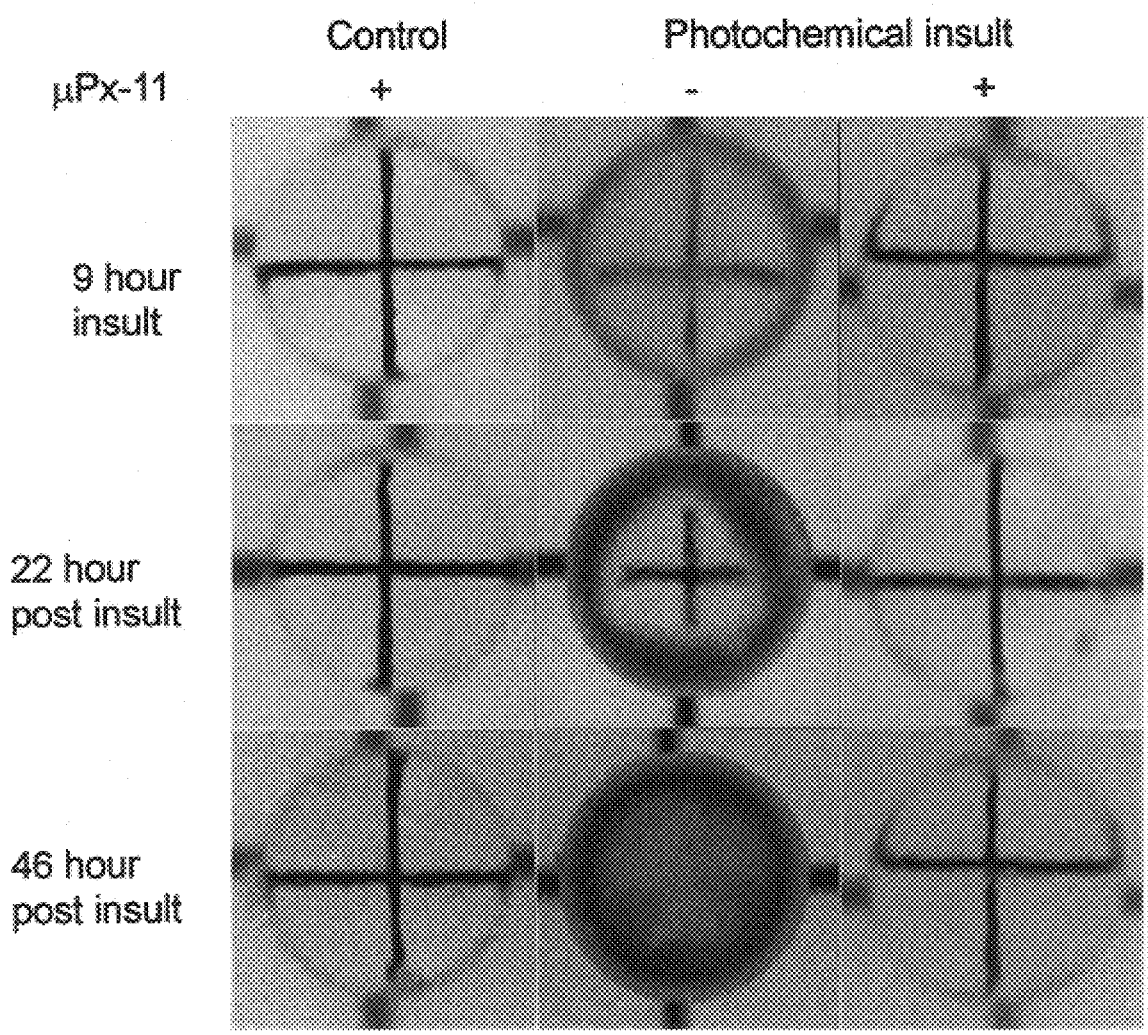

FIG. 8. The effect of $\mu Px$-11 on rat lenses exposed to photochemical insult.

Rat lenses were subjected to photochemical insult as described in the Materials and Methods section hereinbelow. Following a 9 hour insult (three cycles of 3 hour exposures with 4 $\mu M$ riboflavin, 4% $O_2$±5 $\mu M$ $\mu Px$-11), some of the lenses were examined and others incubated for additional post insult periods of 22 hours and 46 hours under normal conditions. Control lenses were incubated with 5 $\mu M$ $\mu Px$-11, 4 $\mu M$ riboflavin in the dark. The lenses were photographed by placing the cluster plates containing the lenses on a transparent grid with illumination from below.

FIG. 9. Trypan blue stained epithelia from lenses subjected to photochemical insult with and without 5 $\mu M$ $\mu Px$-11.

Lenses comparable to those shown in FIG. 8 were washed with isotonic saline and stained with 0.4% Trypan blue for 10 minutes, then washed again with isotonic saline. The capsule-epithelium was then removed, flat mounted, photographed and the percent stained cells determined (see Table 1). Both central and equatorial regions were examined. Characteristic sections from lenses subjected to a 9 hour insult or 22 hour and 46 hour post-insult conditions are shown. See Materials and Methods for further information.

Figure 10:
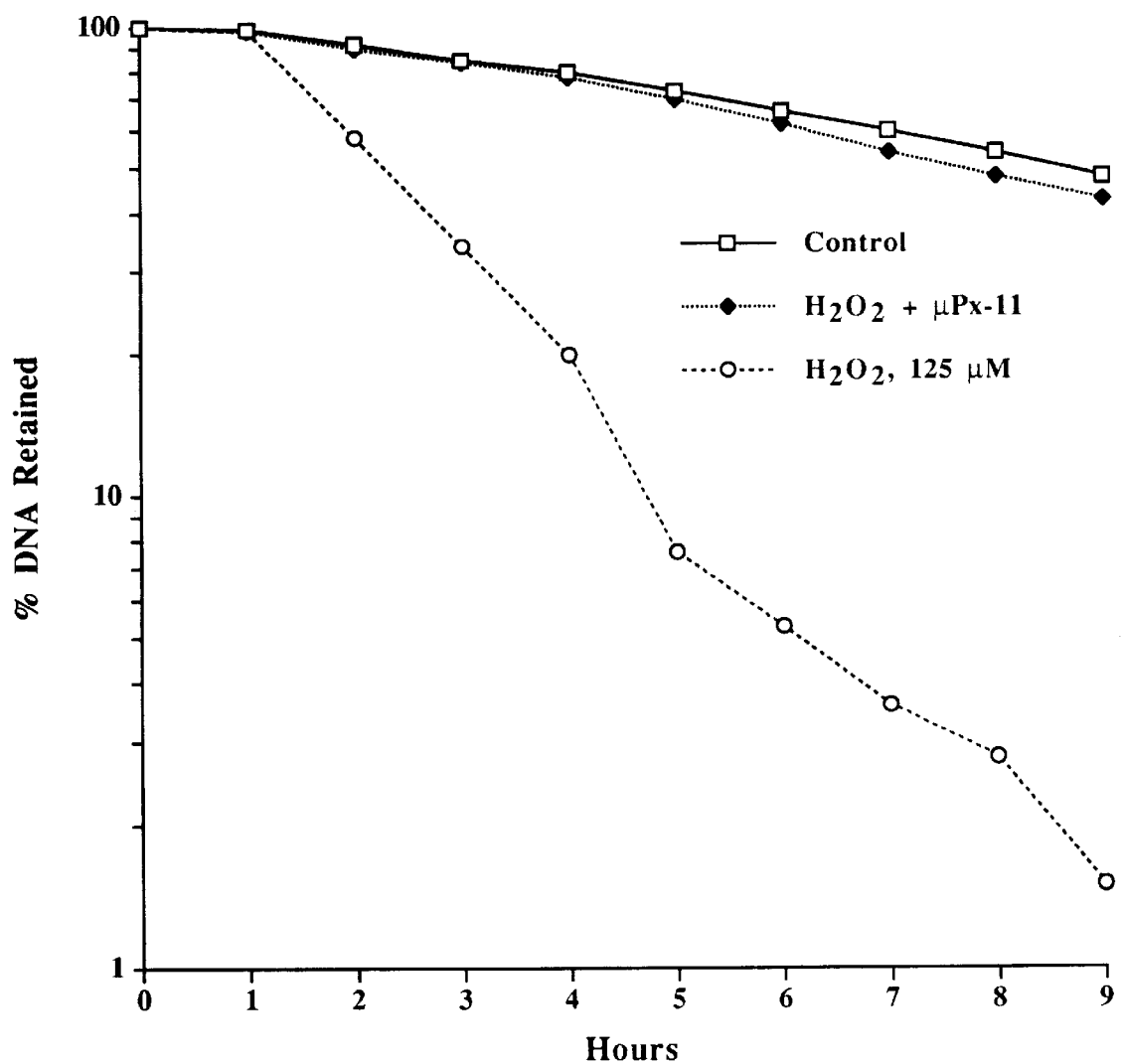

FIG. 10. Alkaline elution of αTN4-1 DNA.

Confluent αTN4-1 cells following labeling with [$^3$H] thymidine were subjected to 125 $\mu M$ $H_2O_2$ in 2 ml Eagles MEM in the presence and absence of 10 $\mu M$ $\mu Px$-11. Following exposure for 3 minutes, the cells were incubated for an additional 5 minutes in MEM containing 20 $\mu g$/ml catalase and then prepared for alkaline elution as described in the Materials and Methods section. Control—cells incubated in Eagles MEM, 125 $\mu M$ $H_2O_2$+10 $\mu M$ $\mu Px$-11, 125 $\mu M$ $H_2O_2$. The figure shows representative results of a typical experiment.

DETAILED DESCRIPTION OF THE INVENTION

This invention provides a method for treating a condition associated with oxidative stress in a subject which comprises administering to the subject an amount of a heme-peptide effective to treat the condition associated with oxidative stress in the subject. The subject may be a mammal. The mammal may be a human being. The condition associated with oxidative stress may be an inflammatory condition, an allergic condition or an auto-immune condition. The invention also provides for a method for treating a condition associated with oxidative stress in a subject which comprises administering to the subject an amount of a heme-peptide and a reducing agent effective to treat the condition associated with oxidative stress in the subject.

As used herein, "condition associated with oxidative stress" encompasses inflammatory conditions and disorders; arthritis, ischemia, osteoarthritis, rheumatoid arthritis, ischemia, cataract, glaucoma, corneal pathology, retinal degeneration, vitreal degeneration, cancer, immune deficiency, hyperimmunity, autoimmunity, neurodegeneration, aging, Alzheimer's disease, Huntington's disease, Machoado-Joseph disease, multiple sclerosis, muscular dystrophy, Parkinson's disease, senility, muscular atrophy, stroke, hepatopathies, systemic lupus erythematosus, mixed connective tissue disease, multiple sclerosis or diabetes.

As used herein, "heme-peptide" encompasses Hemepeptide, heme-peptide, heme-octapeptide, heme-nonapeptide, heme-unadecapeptide, ferriheme-undecapeptide, microperoxidase, 8-microperoxidase, 9-microperoxidase, 11-microperoxidase, a degradation product of cytochrome C, a heme-protein, a synthetic heme-peptide, a heme-peptide analog, a heme-peptide variant, a heme-peptide mimetic, an agent which has the biological activity of a heme-peptide. Heme-peptide may also include a degradation product of a metal porphyrin such as metal containing porphyrin or proto-porphyrin 9. The heme-peptide may include a compound that binds iron or other metal ion. It may also include any compound that has an anti-oxidant property like heme-peptide. One of skill in the art would know which other compounds could be utilized in the present invention. For example, porphyrins have been studied by those of skill in the art, see Chapter 10 of White, Handler, Smith and Stetten, "Principles of Biochemistry" (1959) 2nd. Edition, McGraw Hill Publishing Company.

For the purposes of this invention, "administration" means any of the standard methods of administering a pharmaceutical composition known to those skilled in the art. Examples include, but are not limited to, eye drops, intravenous, intraperitoneal or intramuscular administration.

An "effective amount" of the pharmaceutical composition is any amount of the pharmaceutical composition effective to inhibit or ameliorate conditions due to oxidative stress in the subject. Methods of determining an "effective amount" are well known to those skilled in the art and depend upon a number of factors including, but not limited to: the type of subject involved, the type of condition to be treated. An effective amount of a reducing agent to be present with the heme-peptide is an amount sufficient for the heme-peptide not to degrade and for the heme-peptide to act in an anti-oxidative manner.

In one embodiment of this invention, the animal is a mammal, e.g., a mouse or a human. Preferably, the mammal is a human.

"Administering" means any of the standard methods of administering a pharmaceutical composition known to those skilled in the art. Examples include, but are not limited to eye drops, intravenous, intramuscular or intraperitoneal administration.

In one embodiment of the present invention the amount of heme-peptide comprises from about 10 $\mu$g/kg body weight to about 1 mg/kg body weight. The administration comprises irrigation, intralesional, intraperitoneal, intramuscular or intravenous injection; liposome-mediated delivery; viral infection; gene bombardment; eye drops; topical, nasal, oral, anal, ocular or otic delivery. The heme-peptide may be administered over the life of the subject. The heme-peptide may be administered for about one year to about five years. The heme-peptide may be administered for about one month to about eleven months. The heme-peptide may be administered for about one week to about four weeks.

In another embodiment, the administration of heme-peptide comprises a dosing regime. The dosing regime may comprise a dose of about 1 $\mu$g/kg body weight to about 10 mg/kg body weight twice daily.

The present invention also provides for a method for inhibiting cataract formation in a subject which comprises administering to the subject an amount of heme-peptide effective to inhibit cataract formation in the subject. The heme-peptide may be administered with a reducing agent. The subject may comprise a mammal. The subject may be a dog, a cat, a pig, a cow, a horse, a fowl, a fish, or a human being. The heme-peptide may include a heme-octapeptide, heme-nonapeptide, heme-unadecapeptide, ferriheme-undecapeptide, microperoxidase, 8-microperoxidase, 9-microperoxidase, 11-microperoxidase, a degradation product of cytochrome C, a heme-protein, a synthetic heme-peptide, a heme-peptide analog, or a heme-peptide variant.

The amount of heme-peptide administered may range from about 10 $\mu$g/kg body weight to about 1 mg/kg body weight. The administration may be effected through irrigation, liposome-mediated delivery, viral infection, eye drops, gene bombardment, topical, or ocular delivery. The heme-peptide may be administered over the life of the subject as a preventative measure. The heme-peptide may be administered only for so long as to eradicate any symptoms of the condition. The administration of heme-peptide may comprise a dosing regime. The dosing regime may comprise a dose of about 1 $\mu$g/kg body weight to about 1 mg/kg body weight twice daily for about one day to about 30 days.

Another embodiment of the present invention is a method for inhibiting inflammation in a subject undergoing eye surgery which comprises administering to the subject an amount of a heme-peptide effective to inhibit inflammation in the subject. The heme-peptide may be administered with an appropriate reducing agent. The administration may comprise irrigation, liposome-mediated delivery, viral infection, eye drops, gene bombardment, topical, or ocular delivery. The irrigation may include irrigation before, during and after the surgery or any combination thereof. The subject may comprise a mammal.

The heme-peptide may include heme-octapeptide, heme-nonapeptide, heme-unadecapeptide, ferriheme-undecapeptide, microperoxidase, 8-microperoxidase, 9-microperoxidase, 11-microperoxidase, a degradation product of cytochrome C, a heme-protein, a synthetic heme-peptide, a heme-peptide analog, a heme-peptide variant. The amount of heme-peptide administered may comprise from about 1 $\mu$g/kg body weight to about 10 mg/kg body weight. The heme-peptide may be administered over about 12 hours to about 30 days. The administration of heme-peptide may comprise a dosing regime. One example of a dosing regime may include a dose of about 10 $\mu$g/kg body weight to about 10 mg/kg body weight twice daily for about one day to about 45 days.

Another embodiment of the subject invention is a method for ameliorating eye disease in a subject which comprises administering to the subject an amount of a heme-peptide effective to ameliorate the eye disease in the subject. The subject may comprise a mammal. The mammal may comprise a human being.

The eye disease may comprise an inflammatory eye disease, blindness, cataract, cancer, retinal degeneration, vitreal degeneration, eye degeneration from oxidative stress, neurodegeneration, an allergic eye disease or an auto-immune eye disease. The heme-peptide may include heme-octapeptide, heme-nonapeptide, heme-unadecapeptide, ferriheme-undecapeptide, microperoxidase, 8-microperoxidase, 9-microperoxidase, 11-microperoxidase, a degradation product of cytochrome C, a heme-protein, a synthetic heme-peptide, a heme-peptide analog, a heme-peptide variant.

The amount of heme-peptide administered may comprise from about 1 $\mu$g/kg body weight to about 10 mg/kg body weight. The administration may include irrigation, liposome-mediated delivery, viral infection, eye drops, gene bombardment, topical, or ocular delivery. The heme-peptide may be administered over the life of the subject. The administration of heme-peptide may comprise a dosing regime. One example of a dosing regime may be a dose of about 1 $\mu$g/kg body weight to about 10 mg/kg body weight twice daily for about 6 hours to about 60 days.

The present invention provides for a pharmaceutical composition comprising a heme-peptide and a reducing agent. The heme-peptide of the pharmaceutical composition may include heme-octapeptide, heme-nonapeptide, heme-unadecapeptide, ferriheme-undecapeptide, microperoxidase, 8-microperoxidase, 9-microperoxidase, 11-microperoxidase, a degradation product of cytochrome C, a heme-protein, a synthetic heme-peptide, a heme-peptide analog, a heme-peptide variant. The heme-peptide may also comprise a mixture of heme-peptides. The heme-peptide may be a heme-peptide mimetic.

The reducing agent of the pharmaceutical composition may include ascorbic acid, thioredoxin, glutaredoxin, or coenzyme A reductase. The reducing agent may include an agent or compound or molecule that has a similar reducing potential as ascorbic acid. The reducing agent may be a natural compound or a synthetic compound.

The pharmaceutical composition further comprises a pharmaceutically acceptable carrier. The carrier comprises a diluent. The carrier may also comprise an appropriate adjuvant, a herpes virus, an adenovirus, a liposome, a microencapsule, a polymer encapsulated cell or a retroviral vector.

The pharmaceutically acceptable carrier may be an aerosol, intravenous, oral or topical carrier.

For the purposes of this invention "pharmaceutically acceptable carriers" means any of the standard pharmaceutical carriers. Examples of suitable carriers are well known in the art and may include, but not limited to, any of the standard pharmaceutical carriers such as a phosphate buffered saline solutions, phosphate buffered saline containing Polysorb 80, water, emulsions such as oil/water emulsion, and various type of wetting agents. Other carriers may also include sterile solutions, tablets, coated tablets, and capsules.

Typically such carriers contain excipients such as starch, milk, sugar, certain types of clay, gelatin, stearic acid or salts thereof, magnesium or calcium sterate, talc, vegetable fats or oils, gums, glycols, or other known excipients. Such carriers may also include flavor and color additives or other ingredients. Compositions comprising such carriers are formulated by well known conventional methods.

Such carriers are well known in the art and may include, but not intended to be limited to, any of the standard pharmaceutical carriers such as a phosphate buffered saline solutions, water, emulsions such as oil/water emulsion, and various types of wetting agents. Other carriers may also include sterile solutions, tablets, coated tablets, and capsules.

The heme-peptide molecules of the subject invention also include heme-peptides which are coded for by polypeptide analogs, fragments or derivatives of polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs wherein one or more amino acid residues is added to a terminal or medial portion of the polypeptides) and which share some or all properties of naturally-occurring forms. These include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

Thus, a pharmaceutical composition comprising the soluble protein and a pharmaceutically acceptable carrier is also provided. "Pharmaceutically acceptable carriers" means any of the standard pharmaceutically acceptable carriers. Examples include, but are not limited to, phosphate buffered saline, physiological saline, water and emulsions, such as oil/water emulsions.

The present invention provides that specific proteolytic degradation products of cytochrome C have a high level of peroxidase-like activity and can be stabilized by a group of reductants such as ascorbic acid and NADPH. These compounds degrade $H_2O_2$ and lipid peroxides rapidly in the 1–5 $\mu M$ range and have been shown to protect the lens from developing cataract when subjected to a complex photochemical stress. The compounds appear to be nontoxic based on studies on the cellular and organ level. They are also attractive compounds for use in a variety of eye diseases involving oxidation as well as certain surgical procedures (e.g. vitrecotomy) where oxidation is believed to cause postoperative pathology. The compounds may be helpful in increasing the success of other procedures where the pathology causing the breakdown involves oxidation and perhaps other oxidation associated pathologies, such as joint replacement. The present invention includes an anticataract drug, a compound useful as an addition to solutions used during eye surgery and as a drug to prevent or control certain diseases of the eye and other tissues involving oxidative stress such as inflammation and cytokine and immune responses. The present invention includes a method of treating other disorders due to oxidative stress and physical manifestations of oxidative stress such as arthitis, inflammatory diseases, ischemia, etc., as described herein.

The peroxidase activity of the compounds has been known for more than 30 years. It was first used by histologists in procedures where diaminobenzidine is oxidized to osmiophilic compounds for localization of cells by electron microscopic techniques. While activity of these compounds was recognized, no reports applying these compounds for protection of tissues from oxidative stress had been published. However, the present invention demonstrates that upon stabilization of the compounds with ascorbic acid and other reductants they are useful as anti-oxidants. Cytochrome C is a natural product. It is a protein of about 12 kilodaltons in size. Cytochrome c contains a heme group and may be degraded into a heme-peptide of 8–11 amino acids By adding ascorbic acid or some stabilizing or reducing agent to the heme-peptide of cytochrome C there is a new composition produced.

This invention is illustrated in the Experimental Details section which follows. These sections are set forth to aid in an understanding of the invention but are not intended to, and should not be construed to, limit in any way the invention as set forth in the claims which follow thereafter.

Experimental Details

The present invention provides a compound which prevents cataract associated with oxidative stress (probably ⅓ of the population presenting with maturity onset cataract). It is estimated that approximately 1.5 million cataract operations are performed annually in the United States alone and most are in the maturity onset category. There are approximately 3 fold more people who have been diagnosed as developing cataract. It is predicted that these numbers will increase at least 2 fold over the next decade. Worldwide, the problem is equally severe if not more so. Currently, there is no effective anti-cataract drug available. Surgery is the only remedy for cataract conditions and disorders at the present time. The surgical complication rate during cataract surgeries is 3% (about 45,000 people per year in the United States). A nonsurgical procedure would be desireable and is provided by the present invention. Previous attempts to develop enzyme mimics have failed because of toxicity. Attempts may have been made to develop other types of anti-inflammatory compounds but are not effective in metabolizing $H_2O_2$.

Heme-peptides known as microperoxidase can function as peroxidases, i.e. eliminate peroxides, and since peroxides are central to oxidative stress, alleviate stress. However, in order to eliminate an oxidant by reducing it, there is also an oxidation reaction. In other words, oxidation and reduction reactions are always coupled, one cannot occur without the other. In the case of the microperoxidase, the elimination of peroxides by reduction reactions required an oxidation step. This oxidation was recognized as being deleterious to the system. Thus, microperoxidases were never considered as a treatment for disease processes.

However, as described herein, it is possible to add certain compounds or components to the system to protect it from the oxidation reaction. These components are not obvious since some of them will inactivate the microperoxidase and other are not suitable since they will not react with microperoxidases. As described herein, ascorbic acid, vitamin C, eliminates the cytotoxicity of the microperoxidase and causes it to become a more effective peroxidase with little loss of activity over a period of days.

It has been demonstrated that $H_2O_2$ degradation with catalase prevents the lens from developing cataract and has led to the consideration of using this and other enzymes as the basis for developing $H_2O_2$ degrading enzyme mimics. The present invention requires very low concentrations in order to be effective locally, it is derived from a natural product, it is shown to be nontoxic and acts as an ezyme. It is an enzyme mimic.

Microperoxidases Catalytically Degrade Reactive Oxygen Species and May be Effective Anti-Cataract Agents As described herein, it has been found that a heme-peptide derived from cytochrome C may be an effective, nontoxic $H_2O_2$ degrading agent. Cytochrome C has little peroxidase activity (Paléus, Ehrenberg and Tuppy, 1955). However, following digestion with pepsin (Tsou, 1951), it was shown that a peptic peptide had considerable peroxidase activity (Paléus, Ehrenberg and Tuppy, 1955). Other peptides derived from cytochrome C by the action of varied proteases such as trypsin (Tuppy and Paléus, 1955) and nagarse or with pepsin plus trypsin (Baba, Mizushima and Watanabe, 1969) also were found to have significant peroxidase activity. The active compound obtained by peptic digestion was found to be the ferriheme-undecapeptide shown below (SEQ I.D. No. 1) corresponding to residues 11 to 21 of the parent compound (Tuppy and Paléus, 1955).

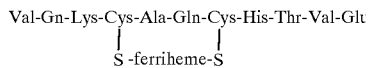

It is covalently linked to the heme by thio ethers. Additional treatment with trypsin removes the N-terminal tripeptide Val-Gln-Lys leaving a heme-octapeptide which is also active. The $His^{18}$ provides an imidizole group which is believed to be coordinated to the porphyrin ferric ion in neutral and alkaline solution (Theorell, 1956; Harbury and Loach, 1960a, 1960b) with $H_2O$ occupying the remaining position. In this disclosure, it is demonstrated that the heme-undecapeptide is capable of protecting rat lenses in organ culture from $H_2O_2$ induced loss of transparency. These heme-peptide peroxidases have been given the name microperoxidase ($\mu$Px) (Feder, 1970).

$\mu$Px-11, a ferriheme-undecapeptide proteolytic degradation product of cytochrome C is shown to be a peroxidase with broad specificity degrading $H_2O_2$ and tertiary butyl hydroperoxide. It is also capable of effectively eliminating superoxide and hydroxyl radical. The peroxidase loses activity in the presence of peroxide unless it is stabilized by ascorbate (Asc) or solutions such as aqueous humor or medium 199. While thiol but not disulfides inactivates the $\mu$Px-11, it is not inhibited in the presence of the rat lens which has a high GSH content. $\mu$Px-11 at concentrations 10 to 50 fold greater than are required to achieve good protective activity exhibits no toxicity based on cell viability, ATP levels and lens transparency after long-term incubations of $\alpha$TN4-1 cells or cultured rat lens.

The peroxidase is capable of protecting cultured rat lenses from photochemical stress where $H_2O_2$, $O_2.^-$ (superoxide) and OH. (Hydroxy radical) are generated based on transparency, choline transport, epithelial cell viability and protein integrity as indicated by SDS-PAGE of the rat lens protein. In the absence of the peroxidase, extensive epithelial cell death and other degradative changes are observed. The DNA of $\alpha$TN4-1 cells can also be protected from $H_2O_2$ induced single strand breaks by the $\mu$Px-11. The overall results as described herein suggest that a number of cytochrome C proteolytic degradation products are peroxidases which may be effective anti-cataract agents protecting the lens from oxidative stress.

$\mu$Px-11 Degrades Reactive Oxygen Species

Materials and Methods $\mu$Px-11, $\mu$Px-8, ascorbic acid, glutathione and other biochemicals were obtained from Sigma Chemical Company, St. Louis, Mo. Chemicals of the highest purity available were used in all experiments.

Assay of Oxidants $H_2O_2$ was assayed by the method of Hildebrandt et al. (1978), as modified by Spector et al. (1993a) and is based on the oxidation of ferroammonium sulfate in the presence of potassium thiocyanate. Superoxide was measured as previously reported (Spector et al., 1993a) by following the reduction of ferricytochrome C in the presence and absence of superoxide dismutase (SOD) as described by Flohé and Otting (1984). The superoxide was generated with the xanthine, xanthine oxidase system utilizing 50 $\mu$M xanthine and 15 mU xanthine oxidase in 0.5 ml containing 50 mM phosphate buffer pH 7.0 and 0.1 mM EDTA and 25 $\mu$M ferricytochrome C. 50 U of SOD was used to eliminate the superoxide. The change in 550 nm absorption was used to follow the reaction utilizing a $\Delta E_M$ at 550 nm of $2.1 \times 10^4$ (Massey, 1959). Hydroxyl radical was determined as previously described (Spector et al., 1993a). The hydroxyl radical was generated by three procedures by modification of the methodology of Halliwell and Gutteridge (1984). Method 1 contained a hypoxanthine/xanthine oxidase/$FeCl_3$ generating system with 0.2 mM hypoxanthine, 16 mU xanthine oxidase, 0.1 mM $FeCl_3$ in 2 ml of 150 mM phosphate buffer pH 7.4, and 0.3 mM EDTA with 2.5 mM salicylate as a trapper. Method 2 utilized ascorbate (Asc) as a radical generator with 0.5 mM Asc, 0.1 mM $FeCl_3$ and 2.5 mM salicylate in the same buffer as in method 1 and in method 3. 0.2 mM $H_2O_2$ was added to the solution used in method 2. The 2,3 dihydroxybenzoate was assayed as previously described (Halliwell and Gutteridge, 1984).

Rat Lens Incubations

Sprague Dawley rats, 5 to 6 weeks old weighing 100 to 120 gm were used. The animals were sacrificed by $CO_2$ inhalation following guidelines cited in the Care and Use of Animals DHEW publication, (WIH 86-23). The eyes were removed and the lenses dissected with a posterior approach and individually incubated in 24 well cluster plates at 37° C. in 1.5 ml of medium 199 with Earle's salts minus phenol red (Sigma M3769) and supplemented with Hepes, 25 mM; glutamine, 100 mg/L and $NaHCO_3$, 0.9 gm/L to give a pH of 7.0 (after equilibration with a 5% $CO_2$ atmosphere) and an osmolarity of 300±3 mosmols. Streptomycin 50 $\mu$g/ml and penicillin 50 U/ml were added to prevent bacterial contamination. Lenses were incubated overnight in 5% $CO_2$ at 37° C. to detect injury occurring during dissection. If the lenses lose their transparency, they are not used. Approximately 10 to 15% of the lenses were eliminated.

Polyacrylamide Gel Electrophoresis of Rat Lens Protein

Rat lenses were incubated in 150 $\mu$l of medium 199 as described above with 20 $\mu$M $\mu$Px-11 present in certain cases. The incubations were carried in an incubator in 5% $CO_2$ 37° C. Also, as indicated, 1 mM Asc was added. Incubations were continued for 24 hours before initiating the experiment.

The lenses were then placed in 2 ml of fresh medium 199 with the same composition as above except that where $\mu$Px-11 was used, the concentration was lowered to 5 $\mu$M. The experiment was initiated by the addition of $H_2O_2$ to give a final concentration of 300 $\mu$M. After thirty minutes, the media was removed and the lenses were quickly washed with isotonic saline and then homogenized at 0° C. in 0.5 ml of 20 mM phosphate pH 7.0. The homogenates were centrifuged at 14,000 rpm at 4° C. for 10 minutes in an Eppendorf model 5402 centrifuge. The supernatant was removed and held at 0° C. while the protein concentration was determined by the Bradford method as described previously (Spector et al. 1996) and then adjusted to 8 mg protein/ml in the phosphate buffer. 100 $\mu$l was then used for SDS polyacrylamide gel electrophoresis (SDS-PAGE) according to Laemmli (1970) as described previously (Wang and Spector, 1994).

The protein preparation was diluted with an equal volume of double concentration sample buffer (125 mM Tris, pH 6.8, 4.6% SDS, 10% 2-mercaptoethanol and 20% glycerol) boiled for 2 minutes and 75 $\mu$g protein applied per lane for SDS-PAGE using 15% cross-linked polyacrylamide slabs. In some cases, 2-mercaptoethanol was omitted. In some experiments, rat lens soluble protein 3 mg/ml in phosphate buffer 10 mM pH 7.0 was directly challenged with $H_2O_2$ 200 $\mu$M with and without 4 $\mu$M $\mu$Px-11 for 30 minutes and then treated as described above. The slabs were stained with Coomassie brilliant blue G.

Photochemical Oxidation of Rat Lenses

The rat lenses were exposed to photochemical stress as previously described (Spector et al., 1993b). 4 $\mu$M riboflavin was used as a photosensitizer. The photo-oxidation was continued for 3 hours and then fresh medium similar to the initial medium was added and the procedure repeated 2 more times. Some of the lenses were then taken for photography and for Trypan blue staining. Incubation of other lenses were continued in the absence of photo-oxidative stress utilizing the normal medium for an additional 22 hours and following exchange with fresh medium for another 24 hours and then taken for photography or Trypan blue staining. In some experiments, the incubations were extended to 65 hours.

Other Biochemical Parameters

ATP was measured as previously described utilizing a bioluminescent procedure (Spector et al., 1993b) and [$^{14}$C] choline uptake was determined as reported by Spector et al. (1993b).

Trypan Blue Staining

The lenses were washed in isotonic saline and were stained with 1.5 ml of a 0.4% Trypan blue solution (Sigma T-8154) for 10 minutes. They were then washed with isotonic saline. The capsule epithelium was removed and flat mounts prepared. Usually 3 fields with about 300 cells were used to determine the percent of stained cells.

Alkaline Elution

Single strand breaks in the DNA of $\alpha$TN4-1 cells which had incorporated [$^3$H]thymidine were determined in the following manner. 35,000 $\alpha$TN4-1 cells were plated on 35 mm Petri dishes with Eagles MEM (Gibco 410-1500) supplemented with 20% fetal calf serum (FCS). Following a 24 hour incubation, the medium was replaced with an identical solution containing 1 $\mu$M thymidine and 0.2 $\mu$Ci/ml. [$^3$H]thymidine. 24 hours later, the cells were confluent and the plates contained approximately 140,000 cells. The medium was again replaced with fresh medium now containing 10 $\mu$M thymidine and incubated an additional 24 hours. The medium was replaced with fresh medium without FCS and after 5 minutes, the cells were subjected to oxidative stress as described elsewhere. The alkaline elution was then performed as described previously (Spector et al., 1989) utilizing the method of Kohn et al. (1976)

Figure 1A:
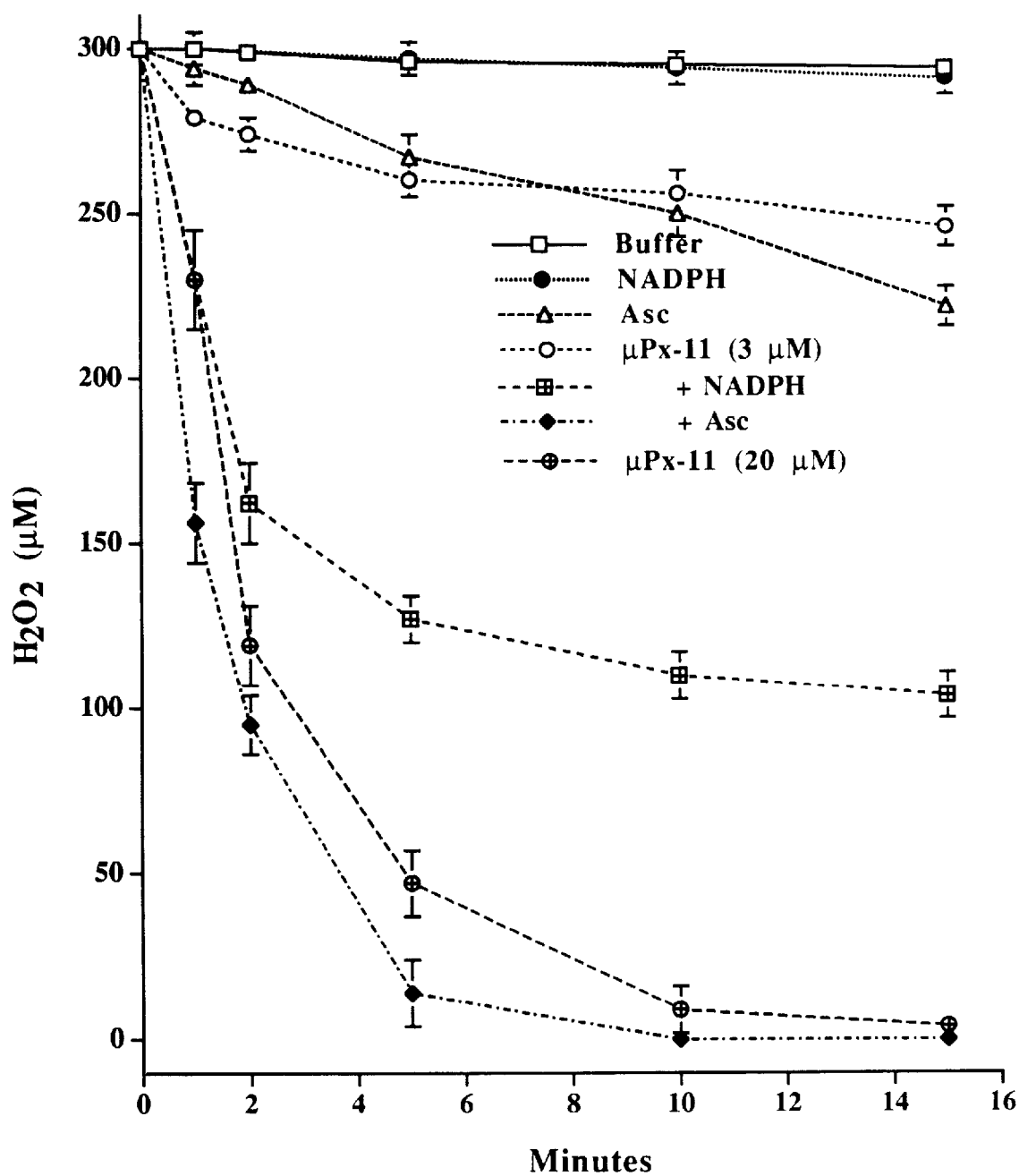

Results $\mu$Px-11 Activity and Stability: Effect of Asc, NADPH and $H_2O_2$ Concentration Examination of the ability of $\mu$Px-11 to degrade $H_2O_2$ is shown in FIG. 1A. At a concentration of 3 $\mu$M, the $\mu$Px-11 has little activity in phosphate buffer, pH 7.0. Although in the first two minutes, there is a respectable rate of $H_2O_2$ degradation, 7.0 nmoles/min/ml/nmole $\mu$Px-11, after this time little activity is observed. The data suggests that the $\mu$Px-11 is rapidly inactivated. At a concentration of 20 $\mu$M $\mu$Px-11, the inactivation is not apparent because of the rapid degradation of the $H_2O_2$. If 1 mM Asc is added to the preparation with 3 $\mu$M $\mu$Px-11, the activity is markedly increased and the $H_2O_2$ is essentially eliminated within 5 minutes. Under these conditions, an initial rate of $H_2O_2$ degradation of 44.3 nmoles/min/ml/nmole $\mu$Px-11 is observed and no loss of activity is evident. Note that under these conditions, the $H_2O_2$ degradation rate is greater than with 20 $\mu$M $\mu$Px-11 alone. To confirm that the Asc performs a dual function of increasing the $H_2O_2$ degradation rate and also stabilizing the enzymatic activity, further experiments were performed. It was found that in phosphate buffer, pH 7.0, in the absence of $H_2O_2$, the $\mu$Px-11 is relatively stable. However, if $H_2O_2$ is present, as shown in FIG. 1B, again rapid inactivation occurs. To further confirm the $H_2O_2$ induced inactivation, 5 $\mu$M $\mu$Px-11 was exposed to 300 $\mu$M $H_2O_2$ for 20 minutes and the $H_2O_2$ decay was followed. The $H_2O_2$ was then rapidly adjusted back to approximately the original concentration and the $H_2O_2$ decay was again observed. Now, little $H_2O_2$ degradation is observed (FIG. 1B). However, if Asc is present during these experiments, the $\mu$Px-11 is stabilized and there is little loss of $\mu$Px-11 activity as noted with the second addition of $H_2O_2$ (FIG. 1B). Asc alone causes a small but steady degradation of $H_2O_2$. The results shown for $\mu$Px-11+Asc are corrected for the Asc contribution.

When NADPH was used as a cofactor instead of Asc, a rapid degradation of $H_2O_2$ was observed for the first two minutes but then the breakdown of $H_2O_2$ decreased markedly (FIG. 1A). NADPH is oxidized by $H_2O_2$ to an insignificant extent during this period based on change in the NADPH 366 nm absorption or $H_2O_2$ decay in the presence of NADPH. Unlike Asc, NADPH does not appear capable of preventing an irreversible inactivation of the µPx-11. This lack of protection is again shown in FIG. 1B where almost no degradation of $H_2O_2$ is observed during the second exposure to $H_2O_2$.

Figure 1C:
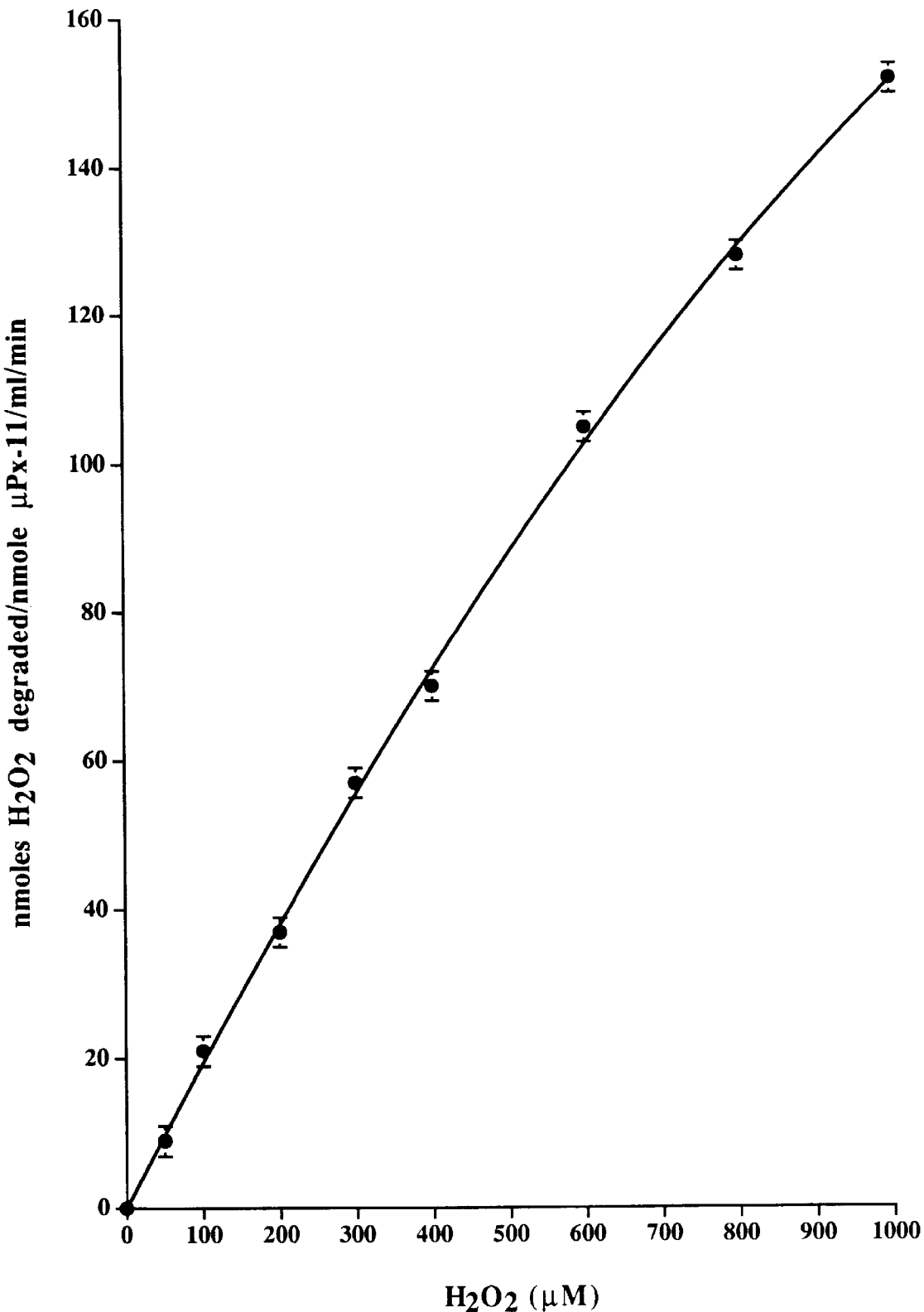

Having established that the µPx-11 is stabilized by Asc, it was of interest to determine the dependency of the µPx-11 activity upon $H_2O_2$ concentration in the presence of 1 mM Asc. As shown in FIG. 1C, the initial degradation rates based on 1 minute values are linear up to about 400 µM $H_2O_2$ and then gradually decrease. Initial rates based on 30 seconds or 2 minutes confirm this conclusion. Of course, all rates are corrected for spontaneous reaction with Asc. Examination of the dependency of the initial rate on Asc concentration indicates that 1 minute rates are constant over the range 400 µM to 1000 µM Asc when 1 µM µPx-11 and 300 µM $H_2O_2$ were used. Because of the spontaneous oxidation of Asc, at lower Asc concentrations, it is difficult to assess the real rate of µPx-11 induced $H_2O_2$ degradation. However, rapid 30 second determinations suggest that even with 100 µM Asc, the initial rate is about the same as at higher concentrations. Thus, it is only to maintain a reasonable Asc concentration for supporting the µPx-11 activity that levels of Asc considerably greater than the $H_2O_2$ concentration are necessary. The Asc dependency results also suggest that the falloff in initial rate observed at higher $H_2O_2$ concentrations is not due to a depletion of Asc but rather to the µPx-11 which may either be approaching substrate saturation and/or reflecting $H_2O_2$ induced inactivation.

Effect of Various Incubation Media on µPx-11 Activity

Figure 2:
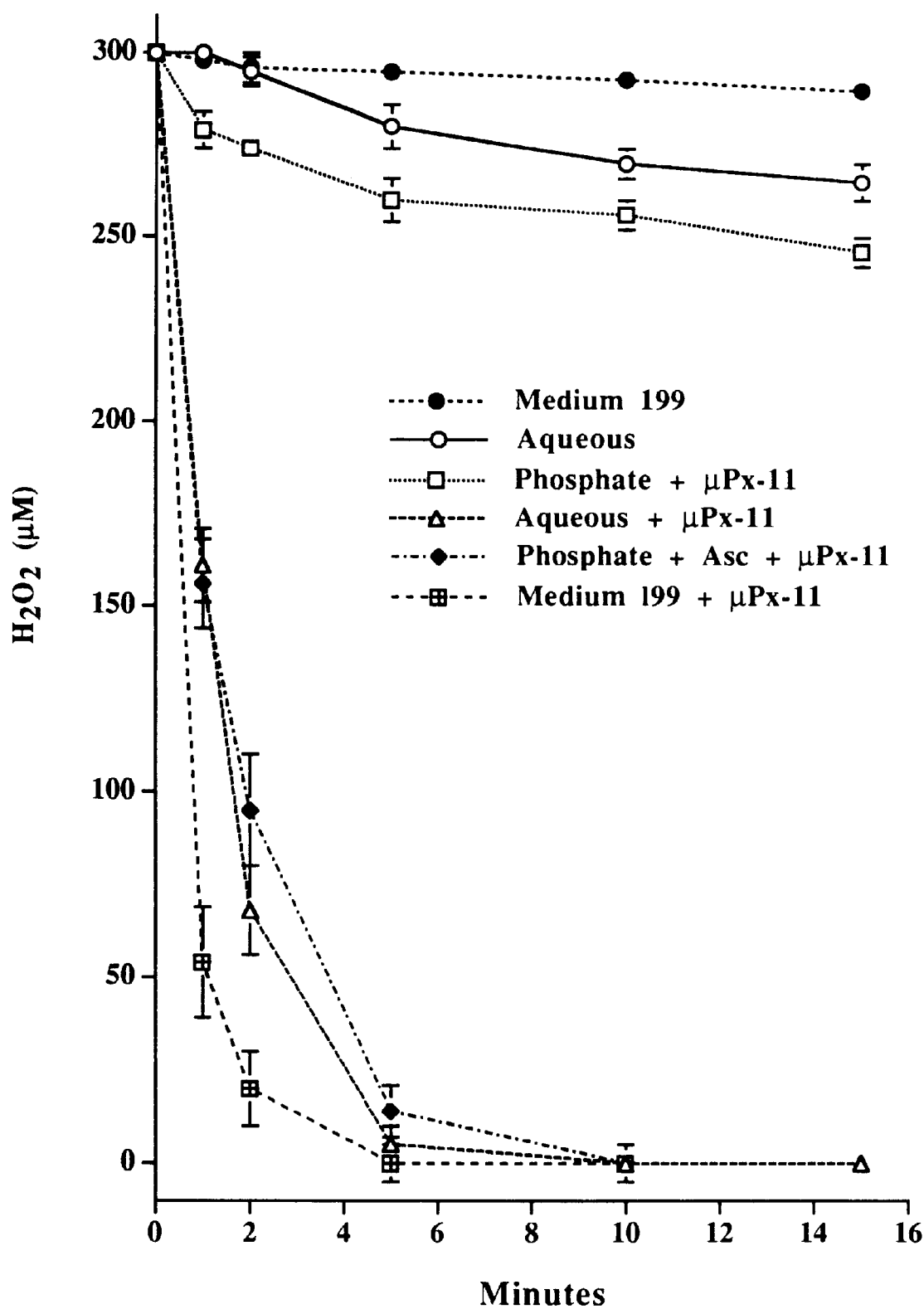
FIG. 2. Effect of different media on $\mu Px$-11 activity.

The µPx-11 activity was also examined with two other media, the aqueous humor which is present in the anterior chamber of the eye and medium 199 containing 25 mM Hepes, pH 7.0 which is frequently used for lens incubations. The aqueous has high concentrations of Asc in the order of 1 mM and medium 199 contains about 0.3 µM Asc. As shown in FIG. 2, the aqueous fluid is as effective as phosphate plus Asc in stimulating µPx-11 activity. Surprisingly, medium 199 appears to be slightly better than the other two solutions in spite of the very low Asc levels.

Effect of GSH and GSSG on µPx-11 Activity

Since GSH is present in high concentration in the lens and is a good reductant, the question arises as to how GSH would effect µPx-11 activity. In these experiments, 20 µM µPx-11 was used without Asc. With such high concentrations of the peroxidase, inactivation was not observed during the 15 minute degradation of 300 µM $H_2O_2$ (FIG. 1A). However, as shown in FIG. 3A, it was found that GSH markedly inhibited µPx-11 activity and unlike NADPH, did not cause an initial stimulation in activity. Increasing the GSH concentration, increased the inhibition. It is interesting that the inhibition is dependent on the thiol groups since GS-SG had only a small inhibitory effect (FIG. 3A). When 3 µM µPx-11 was subjected to 1 mM GSH in the presence of 1 mM Asc, it was found that the Asc was not able to protect the µPx-11 from the thiol induced inhibition (FIG. 3B). Fresh aqueous humor was also examined. The aqueous humor markedly stimulated µPx-11 activity. However, again the presence of 1 mM GSH caused a marked inhibition in the µPx-11 activity.

Effect of the Lens on µPx-11 Activity

The concentration of GSH in the lens varies but may be higher than 10–12 mM in the outer region. Since it is possible that the µPx-11 may enter the lens, the question of inactivation of the peroxidase becomes important from a physiological perspective. To answer this question, rat lenses were incubated for 24 hours in small volumes of medium 199 containing 150 µl with 20 µM of µPx-11 and 1 mM Asc. 100 µl aliquots were then taken and added to 900 µl of phosphate buffer, pH 7.0 containing 1 mM Asc to ascertain the remaining µPx-11 activity. Similar experiments were carried out in the absence of the lens. As shown in FIG. 4, there is only a moderate loss of µPx-11 activity with a 24 hour incubation in the presence or absence of the lens. The presence of the lens causes a slightly larger loss of activity. This result suggests that either the µPx-11 does not appreciably enter the lens or that the GSH in the lens does not inactivate the µPx-11.

The Dependence of µPx-11 Activity on pH

Examination of the effect of pH on the µPx-11 activity is shown in FIG. 5. Utilizing medium 199 containing 25 mM Hepes, a pH optimum of around 8 was observed. At a physiological pH 7.0, the µPx-11 is within 20% of its maximum activity.

µPx-11 Degrades Tertiary Butylhydroperoxide, $O_2.^-$ (superoxide) and OH. (hydroxy radical)

It was also of interest to consider whether the µPx-11 is capable of hydrolyzing hydroperoxides other than $H_2O_2$. As shown in FIG. 6A, tertiary butyl hydroperoxide (TBHP) is effectively hydrolyzed in medium 199, while in phosphate alone, the peroxidase is quickly inhibited. With either solution alone, essentially no loss of TBHP was observed. Thus, like GSHPx-1 but unlike catalase, µPx-11 has a broad specificity. Results similar to those obtained with medium 199 were observed with aqueous humor or addition of ascorbic acid to phosphate buffer. Overall, the data indicates that µPx-11 hydrolyzes $H_2O_2$ about 5 to 10 fold faster than TBHP.

The ability of µPx-11 to metabolize other reactive oxygen species was also investigated. When superoxide was generated by the xanthine, xanthine oxidase system in a phosphate buffer and the superoxide generated in 3 minutes was trapped by cytochrome C, the presence of 5 µM µPx-11 eliminated the superoxide almost as effectively as SOD (FIG. 6B). However, when a photochemical system was used to generate the superoxide, the µPx-11 was somewhat less effective. Under these conditions, the superoxide was trapped over a 30 minute period starting 30 minutes after initiation of the reaction. With µPx-11 at 5 µM, about a 3 fold decrease in trapped superoxide from 37 to 14 nmoles was observed. The reason for the difference in effect between the systems is not certain but it is probable that in the absence of a µPx-11 stabilizer such as ascorbic acid and in the presence of $H_2O_2$ which is also generated by this system, the µPx-11 loses its ability to metabolize superoxide. Asc was not used in these experiments since it would complicate the interpretation of the results.

The effect of µPx-11 on OH. is shown in FIG. 6C. Three different systems were investigated. With the hypoxanthine, xanthine oxidase, $FeCl_3$ system and trapping the radical with salicylate, 113±6 nmoles were detected in 90 minutes in the absence of µPx-11. With 5 µM µPx-11, almost no hydroxyl radical was observed. Utilizing an Asc, $FeCl_3$ system, somewhat less than a 3 fold decrease in trapped hydroxyl radical was observed in a 30 minute period. If $H_2O_2$ was added to the latter system, the amount of hydroxyl radical trapped increased markedly to more than 320 nmoles in 30 minutes but when µPx-11 was added, only 70 nmoles were observed. It can be concluded from these experiments that the µPx-11 effectively eliminates much of the hydroxyl radical generated under a number of different conditions.

µPx-11 is not Toxic to the Lens or Epithelial Cell Cultures and does not Affect Lens Proteins To examine the potential toxicity of the µPx-11, rat lenses were incubated with 20 µM µPx-11 in medium 199 for four days changing the medium every day. No change in transparency was observed. Experiments with 100 μM μPx-11 for one day gave similar results. αTN-4 lens epithelial cells cultured for 24 hours with 20 μM μPx-11 showed no cell death based on Trypan blue staining as a result of exposure to the peroxidase. Examination of ATP levels of cells treated as described above gave similar results with values of 13.2±0.2 nmoles/$10^6$ cells being observed before and after exposure to the μPx-11. Thus, μPx-11 does not appear to be toxic at the cell or organ culture level.

It has previously been reported that when lens proteins are exposed to $H_2O_2$ concentrations as high as 92 μM in the presence of 3.5 μM μPx-11, extensive cross-linking is observed in the short period of 10 minutes (Bodanes and Zigler, 1983). Therefore, to determine if lens proteins are affected in situ, rat lenses were incubated with or without 20 mM μPx-11 for 24 hours and then were subjected to 300 μM $H_2O_2$ for 30 minutes with and without 5 μM μPx-11 as described in the Materials and Methods section. The lens protein was then analyzed by SDS-PAGE electrophoresis. The gels were overloaded so as to reveal the presence of newly formed components. FIG. 7, lanes 8 to 10, show the results obtained in a typical experiment, lane 8 represents the soluble protein from a control lens, lane 9 contains protein from a lens incubated with 20 μM μPx-11 and then exposed to 300 μM and $H_2O_2$ and 5 μM μPx-11 and lane 10 as in lane 9 plus 1 mM Asc during last 30 minute incubation. No difference in the pattern can be observed in these three gels. $H_2O_2$ alone gave similar results. When soluble rat lens protein was directly used without a 24 hour incubation, a pattern similar to the control lens preparation was observed, lane 4. However, when μPx-11, 4 μM+200 μM $H_2O_2$ was added to the protein preparation for 30 minutes, extensive intermolecular cross-linking was observed as previously reported by Bodanes and Zigler (1983) (lane 5). However, if 0.4 mM Asc, lane 6, or 4 mM GSH, lane 7, are present, then the pattern is similar to controls indicating no effect on the lens protein. As shown in lane 3, μPx-11 in the absence of $H_2O_2$ shows no change. Thus, the μPx-11 effect is a result of oxidation of the peroxidase and its subsequent reaction with the lens proteins. This can be prevented by Asc which stabilizes the μPx-11 or GSH which inactivates it. Since 2-mercaptoethanol was used in the SDS solution during the boiling of the samples before electrophoresis, the observed cross-linking is not due to disulfide formation.

μPx-11 Protects the Cultured Lens from Photochemical Stress

Finally, the ability of the μPx-11 to protect the lens from reactive oxygen species was examined utilizing the photochemical riboflavin system which generates superoxide, hydroxyl radical and $H_2O_2$. The lenses were subjected to three, 3 hour periods of photochemical stress with the medium being changed at the end of each period. Peroxide levels of 160±20 μM were observed at the end of each three hour period without 5 μM μPx-11. If the μPx-11 was included, then no $H_2O_2$ could be detected. Superoxide levels as high as 37 nmoles trapped per 30 minutes were observed in the absence of μPx-11. In the presence of the μPx-11, only low levels of superoxide were detected. Following the insulting period, the lens incubations were continued and at given periods, lenses were removed for analyses.

The appearance of the lenses are shown in FIG. 8. The control lenses show no loss of transparency after a 46-hour post-insult period (5 μM μPx-11 was present during the initial 9-hour incubation). Lenses photochemically stressed show some opacification immediately after the nine-hour insult period which becomes progressively worse during the post-insult time. After 46 hours post-insult, a dark opaque ring is present in the equatorial region and a loss of transparency is observed in the remainder of the outer cortex so that the lines displayed under the lens cannot be detected. In contrast, when 5 μM μPx-11 is present during insult, no loss of transparency can be observed. In some cases, incubations were extended to 65 hours after insult with similar results.

At the end of the insult period and at 22 and 46 hours post-insult, some of the lenses were removed and their epithelia were stained with Trypan blue to check cell viability. Little staining was observed in either the central or equatorial regions of the epithelial cell layer from controls or lenses incubated in the presence of μPx-11 (FIGS. 9A–9C). In contrast, immediately after the insulting period in the absence of μPx-11, most of the equatorial cells and about 25±8% of the cells in the central region are stained (Table I). By 22 hours, almost all cells from lenses not protected by μPx-11 are stained. The cells from lenses protected with μPx-11 continue to show patterns similar to controls at 46 hours post-insult with very little staining in either the equatorial or central regions.

TABLE I

Trypan blue staining of lens epithelial cells

| Post-Insult (Hrs) | | Percent Stained cells | |
|---|---|---|---|
| | | | Photochemical Insult |
| | | control | |
| | epithelium | +μPx-11 | −μPx-11 | +μPx-11 |
| 0 | central | 1–2 | 25 ± 8 | 1–2 |
| | equatorial | 3–4 | 75 ± 10 | 3–4 |
| 22 | central | 1–2 | 80 ± 7 | 1–2 |
| | equatorial | 3–5 | 100 | 3–4 |
| 46 | central | 2–3 | 95 ± 5 | 1–2 |
| | equatorial | 3–5 | 100 | 3–4 |

Staining was examined in the central and equatorial regions of whole mounts of capsule-epithelia from lenses exposed to oxidative stress in the presence or absence of 5 μM μPx-11. For each determination, 3 fields containing a few hundred cells were evaluated. The results are expressed as the average±S.D. of two independent experiments.

[$^{14}$C] Choline uptake was also followed in lenses which were 65 hours post-insult. The control lenses initially gave lens/medium ratios of about 3.5±0.41 and 3.06±0.46 after a 74 hour incubation to conform with the experimental 9 hour insult and 65 hour post-insult period. The insulted lenses showed no concentration of choline (Table II). In contrast, with 5 μM μPx-11, there appears to be no loss in ability to concentrate [$^{14}$C] choline.

TABLE II

Choline uptake of rat lenses following photochemical insult

| | Lens/medium [$^{14}$C] choline | |
|---|---|---|
| Post-insult period | 0 hrs. | 65 hrs |
| control + μPx-11 | 3.50 ± 0.41 | 3.06 ± 0.46 |
| insult − μPx-11 | — | 0.90 ± 0.21 |
| insult + μPx-11 | — | 3.95 ± 0.57 |

Choline uptake was measured following photochemical insult in the presence and absence of 5 μM μPx-11. The μPx-11 was present only during the 9 hour insult period. See the text for further information.

μPx-11 Protects αTN4-1 Cell DNA from $H_2O_2$ Stress

An early effect of $H_2O_2$ stress on biological systems is the generation of single strand DNA breaks (Spector et al., 1989). To ascertain the protective effect of μPx-11, αTN4-1 cells following [³H]thymidine incorporation were subjected to 125 μM $H_2O_2$ in the presence and absence of 10 μM μPx-11. Following a three minute exposure, the medium was removed, the DNA extracted and analyzed for single strand breaks by alkaline elution. In the absence of $H_2O_2$, no significant degradation is observed in the presence or absence of μPx-11 with or without the addition of Asc. Since these results are so similar, a typical control without μPx-11 is shown (FIG. 10). In some experiments, cells were pretreated with 10 μM μPx-11 for 24 hours before initiating the experiment.

No effect was observed as a result of the preincubation. However, $H_2O_2$ in the absence of μPx-11 causes extensive degradation. As shown, this is completely prevented by μPx-11.

Discussion

μPx-11 Protects Lens Systems from Complex Oxidative Stress

It is apparent from this work that μPx-11 is very effective in the low μM range in protecting both lens and epithelial cell cultures from oxidative stress. This protection is observed even when a range of oxidants including OH., $O_2.^-$ and $H_2O_2$ are present. It was previously shown with catalase, that elimination of the $H_2O_2$ is sufficient for protection of the lens system. However, unlike catalase, μPx-11 appears to degrade $O_2.^-$ and OH. as well as $H_2O_2$ increasing its potential protective ability. Unlike the GSHPx mimics, μPx-11 also appears to be non-toxic in the presence of Asc. These characteristics of μPx-11 make it very attractive for preventing oxidative stress induced pathology in the eye since Asc is present in high concentration throughout the tissue.

Mechanism of μPx-11 Action

While the mechanism by which μPx-11 degrades $H_2O_2$ is not understood, it is probable that it acts as a peroxidase with a general mechanism as shown below:

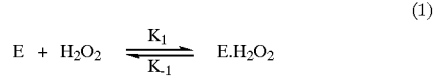
(1)

(2)

In the present application, Asc appears to be a long-term effective reductant. For a short while the μPx-11 may utilize a second molecule of $H_2O_2$ as a reductant leading to the release of $O_2$ (Chance, Sies and Boveris, 1979). However, it is clear from the present investigation that such a reaction quickly leads to inactivation. With Asc as the reductant, the enzyme can quickly cycle large quantities of $H_2O_2$ with a relatively small loss of activity. But the choice of reductant is critical since NADPH activation is only short term and GSH quickly inhibits $H_2O_2$ degradation suggesting that an inactive reduced complex is formed. In this respect, it is interesting that NADPH dependent lipid peroxidation of brain microsomes was found to be inhibited by μPx-11 (Vodnyánsky et al., 1985).

It is also possible to follow the activity of the μPx-11 by observing the change in absorbance at 399 nm. With $H_2O_2$ alone, this absorption peak quickly disappears. However, if 1 mM Asc is present, there is only a small change in 399 nm absorption over a 24 hour period. Thus, the loss of activity can be linked to disappearance of the 399 nm peak. In contrast, reaction with GSH which also quickly inactivates the μPx-11 leads to a rapid shift in absorption to 413 nm which gradually declines over the next few hours. It is probable that the structure with the 413 nm absorption peak has no activity.

It is noted that in spite of the high concentration of GSH in the lens, μPx-11 incubated for 24 hours in the presence of the lens loses little activity. Since the μPx-11 has a relatively small size of 1861 Da, it might be assumed that the μPx-11 enters the lens. Since the incubation medium volume was only 150 μl, it would be expected that a significant decrease in activity would occur if μPx-11 cycled in and out of the tissue over a 24 hour period. Entry into the lens is not necessary for degrading $H_2O_2$. As previously shown with catalase, degrading the $H_2O_2$ outside the lens is sufficient to eliminate $H_2O_2$ within the organ because of the rapid diffusion rate of the $H_2O_2$ (Spector et al., 1993a)

In cytochrome C, the iron in the heme forms axial coordinates with $Met^{80}$ and $His^{18}$ (Takano et al., 1973). In μPx-11, the $Met^{80}$, of course, is no longer present. The imidazole coordination with the heme groups is believed to be retained in μPx-11 and is probably involved in the reaction with $H_2O_2$ (Ehrenberg and Theorell, 1955; Aron et al., 1986). Thus, the ferric ion is believed to be 6-coordinate with the $His^{18}$ and $H_2O$ occupying the axial coordinate sites. It is probable that the reaction is initiated by $H_2O_2$ displacing the $H_2O$. The pH optimum for the μPx-11 is shown in this investigation to be approximately 8.0 with a gradual decrease in activity at higher pH's. Since the $pk_a$ of $H_2O_2$ is 11.8, it is likely that it is $HO_2^-$ that reacts with the μPx-11.

Other Proteolytic Degradation Products of Cytochrome C are Peroxidases

Degradation of cytochrome C by proteolytic enzymes gives rise to a number of products containing the heme group. μPx-8 has the cytochrome C peptide segment containing residue 14 to 21. Thus, the first three residues present in μPx-11 have been eliminated. It can be prepared by subjecting the peptic product of cytochrome C, μPx-11, to extensive tryptic digestion as reported by Kraehenbuhl, Galardy and Jamieson (1974) and Aron et al. (1986). A tryptic degradation of cytochrome C yields μPx-9 in which the peptide component contains a C-terminal lysine addition to the μPx-8 peptide. A number of other μPxs have also been reported (Baba, Mizushima and Watanabe, 1969). All of these cytochrome C degradation products appear to have peroxidative activity (Paléus, Ehrenberg and Tuppy, 1955; Baba, Mizushima and Watanabe, 1969). A comparison between the ability of μPx-8 to degrade $H_2O_2$ with the ability of μPx-11 was carried out. Both peroxidases are inactivated by $H_2O_2$ in the absence of Asc and show the same inhibitory response with GSH. However, in the presence of 1 mM Asc, μPx-8 appears to be more active than μPx-11. It is possible that the positive charge on the E-$NH_2$ group of the Lys in μPx-11 contributes to this difference in activity.

Verification that μPx-11 Quenches $O_2.^-$ (Superoxide)

It is established that cytochrome C is involved in the electron transfer which occurs in the mitochondria shuttling electrons from the cytochrome reductase heme group to that of cytochrome oxidase. It is shown that the μPxs can act in a similar fashion to cytochrome C in oxid/red reactions (Baba, Mizushima and Watanabe, 1969). Furthermore, these workers suggest that μPx-11 slowly oxidize ferrocytochrome C. This raises the possibility that in the measurements of $O_2.^-$ herein in which ferricytochrome C is reduced to ferrocytochrome C, the presence of µPx-11 may simply cause a reoxidation of the ferroheme. To check this possibility, ferrocytochrome C was subjected to the ferriheme µPx-11 under the conditions used to measure $O_2.^-$. The change in the characteristic 550 nm absorption of the ferrocytochrome C was then observed. Little change in absorption was observed over a 10 minute period. Since most of the $O_2.^-$ is generated and trapped within two minutes, the failure to generate 550 nm absorption in the presence of $O_2.^-$ is probably due to electron trapping by the µPx-11. In another experiment, the absorption of the µPx-11 was followed during the generation of $O_2.^-$ at 399 nm, the characteristic absorption maximum of µPx-11. A rapid drop in 399 nm absorption was observed suggesting reduction of the µPx-11. Thus, these experiments confirm that µPx-11 is capable of detoxifying $O_2.^-$.

References

Aron, J., Baldwin, D. A., Marques, H. M., Pratt, J. M. and Adams, P. A. (1986). Hemes and hemoproteins. 1: Preparation and analysis of the heme-containing octapeptide (microperoxidase-8) and identification of the monomeric form in aqueous solution. *J. Inorg. Biochem.* 27, 227–43.

Baba, Y., Mizushima, H. and Watanabe, H. (1969). Catalytic properties of cytochrome C heme peptides. *Chem. Pharm. Bull.* 17, 82–8.

Baldwin, D. A., Marques, H. M. and Pratt, J. M. (1987). Hemes and hemoproteins 5. Kinetics of the peroxidatic activity of microperoxidase-8: Model for peroxidase enzymes. *J. Inorg. Biochem.* 30, 203–17.

Bodanes, R. S. and Zigler, J. S. Jr. (1983). The rapid $H_2O$-mediated nonphotodynamic crosslinking of lens crystallins generated by the heme-undecapeptide from cytochrome C: implications in man. *Biochem. Biophys. Res. Com.* 113, 592–7.

Chance, B., Sies, H. and Boveris, A. (1979). Hydroperoxide metabolism in mammalian organs. *Physiol. Rev.* 59, 527–605.

Ehrenberg, A. and Theorell, H. (1955). On the stereochemical structure of cytochrome C. *Acta Chem. Scand.* 9, Part II, 1193–1205.

Feder, N. (1970). A heme-peptide as an ultrastructural tracer. *J. Histochem. Cytochem.* 18, 911–3.

Flohé, L. and Otting, G. (1984). Superoxide dismutase assays. *Meth. Enzymol.* 105, 101–4.

Halliwell, B. and Gutteridge, J. M. C. (1984). Role of iron in oxygen radical reactions. *Meth. Enzymol.* 105, 47–56.

Harbury, H. A. and Loach, P. A. (1960a) Oxidation-linked proton functions in heme octa- and undecapeptides from mammalian cytochrome C. *J. Biol. Chem.* 235, 3640–45.

Harbury, H. A. and Loach, P. A. (1960b.). Interaction of nitrogenous ligands with heme peptides from mammalian cytochrome C. *J. Biol. Chem.* 235, 3646–53.

Hildebrandt, A. G., Root, I., Tjoe, M. and Heinemeyer, G. (1978). $H_2O_2$ in hepatic microsomes. *Meth. Enzymol.* L11, 342–50.

Kohn, K. W., Erickson, L. C., Ewig, R. A. G. and Friedman, C. A. (1976). Fractionation of DNA from mammalian cells by alkaline elution. *Biochemistry* 15, 4629–37.

Kraehenbuhl, J. P., Galardy, R. E. and Jamieson, J. D. (1974). Preparation and characterization of an immunoelectron microscope tracer consisting of a heme-octapeptide coupled to Fab. *J. Exp. Med.* 139, 208–23.

Laemmli, U. K. (1970). Cleavage of structural proteins during the assembly of the head of bacteriophage T4. *Nature* 227, 680–5.

Massey, V. (1959). The microestimation of succinate and the extinction coefficient of cytochrome c. *Biochim. Biophys. Acta* 34, 255–6.

Paléus, S., Ehrenberg, A. and Tuppy, H. (1955). Study of a peptic degradation product of cytochrome C. II. Investivation of the linkage between peptide moiety and prosthetic group. *Acta Chem. Scand.* 9, 365–74.

Spector, A. (1995). Oxidative stress induced cataract Mechanism of action. *FASEB J.* 9, 1173–82.

Spector, A., Kleiman, N. J., Huang, R-R. C. and Wang, R-R. (1989). Repair of $H_2O_2$ induced DNA damage in bovine lens epithelial cell cultures. *Exp. Eye Res.* 49, 685–98.

Spector, A., Wang, G-M., Wang, R-R., Garner, W. H. and Moll, H. (1993a). The prevention of cataract caused by oxidative stress in cultured rat lenses. I. $H_2O_2$ and photochemically induced cataract. *Curr. Eye Res.* 12, 163–79.

Spector, A., Wang, G-M. and Wang, R-R. (1993b). The prevention of cataract caused by oxidative stress in cultured rat lenses. II. Early effects of photochemical stress and recovery. *Exp. Eye Res.* 57, 659–67.

Spector, A., Yang, Y., Ho, Y-S., Magnenat, J-L., Wang, R-R., Ma, W. and Li, W-C. (1996). Variation in cellular glutathione peroxidase activity in lens epithelial cells, transgenics and knockouts does not significantly change the response to $H_2O_2$ stress. *Exp. Eye Res.* 62, 521–39.

Takano, T., Kallai, O. B., Swanson, R. and Dickerson, R. E. (1973). The structure of ferrocytochrome c at 2.45 A resolution. *J. Biol. Chem.* 248, 5234–55.

Theorell, H. (1956). Nature and mode of action of oxidation enzymes. *Science* 124, 467–72.

Tsou, C. L. (1951). Cytochrome C modified by digestion with proteolytic enzymes. *Biochem. J.* 49, 367–74.

Tuppy, H. and Paléus, S. (1955). Study of a peptic degradation product of cytochrome C. I. Purification and chemical composition. *Acta Chem. Scand.* 9, 353–64.

Vodnyánsky, L., Marton, A., Venekei, I., Végh, M., Blázovits, A., Kittel, A. and Horváth, I. (1985). Inhibition of lipid peroxidation by heme-nonapeptide derived from cytochrome C. *Biochim. Biophys. Acta* 835, 411–4.

Wang, K. and Spector, A. (1994). The chaperone activity of bovine a crystallin: Interaction with other lens crystallins in native and denatured states. *J. Biol. Chem.* 269, 13601–8.

Wendel, A. (1985). European Patent 0-165-534.

Wilson, S. R., Zucker, P. A., Huang, R-R. C. and Spector, A. (1989). A development of synthetic compounds with glutathione peroxidase activity. *J. Am. Chem. Soc.* 111, 5936–9.

What is claimed is:

1. A method for treating a condition associated with oxidative stress in a subject which comprises administering to the subject an amount of a heme-peptide effective to treat the condition associated with oxidative stress in the subject.

2. The method of claim 1, wherein the subject comprises a mammal.

3. The method of claim 2, wherein the mammal comprises a human being.

4. The method of claim 1, wherein the heme-peptide is administered with a reducing agent.

5. The method of claim 1, wherein the condition associated with oxidative stress comprises an inflammatory condition, an allergic condition or an auto-immune condition.

6. The method of claim 1, wherein the condition associated with oxidative stress comprises osteoarthritis, rheumatoid arthritis, ischemia, cataract, corneal pathology, glaucoma, retinal degeneration, vitreal degeneration, cancer, immune deficiency, hyperimmunity, autoimmunity, neurodegeneration, aging, Alzheimer's disease, Huntington's disease, Machoado-Joseph disease, multiple sclerosis, muscular dystrophy, Parkinson's disease, senility, muscular atrophy, stroke, hepatopathies, systemic lupus erythematosus, mixed connective tissue disease, multiple sclerosis or diabetes.

7. The method of claim 1, wherein the heme-peptide comprises heme-octapeptide, heme-nonapeptide, heme-unadecapeptide, ferriheme-undecapeptide, microperoxidase, 8-microperoxidase, 9-microperoxidase, 11-microperoxidase, a degradation product of cytochrome C, a heme-protein, a synthetic heme-peptide, a heme-peptide analog, a heme-peptide variant.

8. The method of claim 1, wherein the amount of heme-peptide comprises from about 10 μg/kg body weight to about 1 mg/kg body weight.

9. The method of claim 1, wherein the administration comprises irrigation, intralesional, intraperitoneal, intramuscular or intravenous injection; liposome-mediated delivery; viral infection; gene bombardment; eye drops; topical, nasal, oral, anal, ocular or otic delivery.

10. The method of claim 1, wherein the heme-peptide is administered over the life of the subject.

11. The method of claim 1, wherein the heme-peptide is administered for about one year to about five years.

12. The method of claim 1, wherein the heme-peptide is administered for about one month to about eleven months.

13. The method of claim 1, wherein the heme-peptide is administered for about one week to about four weeks.

14. The method of claim 1, wherein the administration of heme-peptide comprises a dosing regime.

15. The method of claim 14, wherein the dosing regime comprises a dose of about 1 μg/kg body weight to about 10 mg/kg body weight twice daily.

16. A method for inhibiting cataract formation in a subject which comprises administering to the subject an amount of heme-peptide effective to inhibit cataract formation in the subject.

17. The method of claim 16, wherein the subject comprises a mammal.

18. The method of claim 16, wherein the mammal comprises a human being.

19. The method of claim 16, wherein the heme-peptide comprises heme-octapeptide, heme-nonapeptide, heme-unadecapeptide, ferriheme-undecapeptide, microperoxidase, 8-microperoxidase, 9-microperoxidase, 11-microperoxidase, a degradation product of cytochrome C, a heme-protein, a synthetic heme-peptide, a heme-peptide analog, or a heme-peptide variant.

20. The method of claim 16, wherein the amount of heme-peptide comprises from about 10 μg/kg body weight to about 1 mg/kg body weight.

21. The method of claim 16, wherein the administration comprises irrigation, liposome-mediated delivery, viral infection, eye drops, gene bombardment, topical, or ocular delivery.

22. The method of claim 16, wherein the heme-peptide is administered over the life of the subject.

23. The method of claim 16, wherein the administration of heme-peptide comprises a dosing regime.

24. The method of claim 23, wherein the dosing regime comprises a dose of about 1 μg/kg body weight to about 1 mg/kg body weight twice daily for about one day to about 30 days.

25. A method for inhibiting inflammation in a subject undergoing eye surgery which comprises administering to the subject an amount of a heme-peptide effective to inhibit inflammation in the subject.

26. The method of claim 25, wherein the administration comprises irrigation, liposome-mediated delivery, viral infection, eye drops, gene bombardment, topical, or ocular delivery.

27. The method of claim 26, wherein the irrigation comprises irrigation before, during and after the surgery.

28. The method of claim 25, wherein the subject comprises a mammal.

29. The method of claim 28, wherein the mammal comprises a human being.

30. The method of claim 25, wherein the heme-peptide comprises heme-octapeptide, heme-nonapeptide, heme-unadecapeptide, ferriheme-undecapeptide, microperoxidase, 8-microperoxidase, 9-microperoxidase, 11-microperoxidase, a degradation product of cytochrome C, a heme-protein, a synthetic heme-peptide, a heme-peptide analog, a heme-peptide variant.

31. The method of claim 25, wherein the amount of heme-peptide comprises from about 1 μg/kg body weight to about 10 mg/kg body weight.

32. The method of claim 25, wherein the heme-peptide is administered over about 12 hours to about 30 days.

33. The method of claim 25, wherein the administration of heme-peptide comprises a dosing regime.

34. The method of claim 33, wherein the dosing regime comprises a dose of about 10 μg/kg body weight to about 10 mg/kg body weight twice daily for about one day to about 45 days.

35. A method for ameliorating eye disease in a subject which comprises administering to the subject an amount of a heme-peptide effective to ameliorate the eye disease in the subject.

36. The method of claim 35, wherein the subject comprises a mammal.

37. The method of claim 36, wherein the mammal comprises a human being.

38. The method of claim 35, wherein the eye disease comprises an inflammatory eye disease, blindness, cataract, cancer, retinal degeneration, vitreal degeneration, eye degeneration from oxidative stress, neurodegeneration, an allergic eye disease or an auto-immune eye disease.

39. The method of claim 35, wherein the heme-peptide comprises heme-octapeptide, heme-nonapeptide, heme-unadecapeptide, ferriheme-undecapeptide, microperoxidase, 8-microperoxidase, 9-microperoxidase, 11-microperoxidase, a degradation product of cytochrome C, a heme-protein, a synthetic heme-peptide, a heme-peptide analog, a heme-peptide variant.

40. The method of claim 35, wherein the amount of heme-peptide comprises from about 1 μg/kg body weight to about 10 mg/kg body weight.

41. The method of claim 35, wherein the administration comprises irrigation, liposome-mediated delivery, viral infection, eye drops, gene bombardment, topical, or ocular delivery.

42. The method of claim 35, wherein the heme-peptide is administered over the life of the subject.

43. The method of claim 35, wherein the administration of heme-peptide comprises a dosing regime.

44. The method of claim 43, wherein the dosing regime comprises a dose of about 1 μg/kg body weight to about 10 mg/kg body weight twice daily for about 6 hours to about 60 days.

45. A pharmaceutical composition comprising a heme-peptide and a reducing agent.

46. The pharmaceutical composition of claim 45, wherein the heme-peptide comprises heme-octapeptide, heme-nonapeptide, heme-unadecapeptide, ferriheme-undecapeptide, microperoxidase, 8-microperoxidase, 9-microperoxidase, 11-microperoxidase, a degradation product of cytochrome C, a heme-protein, a synthetic heme-peptide, a heme-peptide analog, a heme-peptide variant.

47. The pharmaceutical composition of claim 45, wherein the heme-peptide comprises a mixture of heme-peptides.

48. The pharmaceutical composition of claim 45, wherein the heme-peptide comprises a heme-peptide mimetic.

49. The pharmaceutical composition of claim 45, wherein the reducing agent comprises ascorbic acid, thyoredoxin, glutoredoxin, or coenzyme A reductase.

50. The pharmaceutical composition of claim 45, wherein the pharmaceutical composition further comprises a pharmaceutically acceptable carrier.

51. The pharmaceutical composition of claim 50, wherein the carrier comprises a diluent.

52. The pharmaceutical composition of claim 51, wherein the carrier comprises an appropriate adjuvant, a herpes virus, an adenovirus, a liposome, a microencapsule, a polymer encapsulated cell or a retroviral vector.

53. The pharmaceutical composition of claim 51, wherein the pharmaceutically acceptable carrier is an aerosol, intravenous, oral or topical carrier.

* * * * *

UNITED STATES PATENT AND TRADEMARK OFFICE
CERTIFICATE OF CORRECTION

PATENT NO. : 6,013,623
DATED : January 11, 2000
INVENTOR(S) : Abraham Spector, et al.

It is certified that error appears in the above-identified patent and that said Letters Patent is hereby corrected as shown below:

column 1, line 4 please insert --The invention disclosed herein was made with Government support under NIH Grant No. EY00423. Accordingly, the U.S. Government has certain rights in this invention.-- column 2, line 4 "FIG. 1B" should read --FIG. 1B-1 and 1B-2-- column 12, line 48 "FIG. 1B" should read --FIG. 1B-1 and 1B-2-- column 12, line 54-55 "FIG. 1B" should read --FIG. 1B-1 and 1B-2-- column 12, line 57-58 "FIG. 1B" should read --FIG. 1B-1 and 1B-2-- column 13, line 2 "FIG. 1B" should read --FIG. 1B-1 and 1B-2--

UNITED STATES PATENT AND TRADEMARK OFFICE
CERTIFICATE OF CORRECTION

PATENT NO. : 6,013,623
DATED : January 11, 2000
INVENTOR(S) : Abraham Spector, et al.

Page 2 of 2

It is certified that error appears in the above-identified patent and that said Letters Patent is hereby corrected as shown below:

column 18, line 60 "Superoxide" should read
--superoxide--

Signed and Sealed this

Fifteenth Day of May, 2001

Attest:

NICHOLAS P. GODICI

Attesting Officer     Acting Director of the United States Patent and Trademark Office